United States Patent [19]

Ours et al.

[11] 4,323,691

[45] Apr. 6, 1982

[54] HYDROXYAMINOMETHYL DERIVATIVES OF BENZOYL DI-SUBSTITUTED α-PHENOXYALKANOYL ESTERS

[75] Inventors: Carroll W. Ours, Zion; Cheuk M. Lee, Libertyville, both of Ill.

[73] Assignee: Abbott Laboratories, North Chicago, Ill.

[21] Appl. No.: 212,007

[22] Filed: Dec. 1, 1980

Related U.S. Application Data

[63] Continuation-in-part of Ser. No. 83,008, Oct. 9, 1979, abandoned.

[51] Int. Cl.[3] .................... C07C 101/34; A61K 31/24

[52] U.S. Cl. .................................... 560/36; 424/319; 424/324; 260/326.4; 260/326.41; 544/58.2; 544/79; 544/82; 544/85; 544/86; 544/87; 544/129; 544/141; 544/154; 544/159; 544/162; 546/189; 546/190; 546/195; 546/204; 546/226; 546/232; 560/9; 560/10; 560/17; 562/427; 562/431; 562/441; 562/451; 564/165; 424/248.52; 424/248.54; 424/267; 424/274; 424/309

[58] Field of Search ........................ 560/9, 36, 17, 10; 562/441, 451, 431, 427; 544/158, 162, 58.2, 79, 82, 85, 86, 87, 129, 154, 159, 141; 546/226, 189, 190, 195, 204, 232; 260/326.5 S, 326.5 E, 326.4, 326.41; 564/162, 165

[56] References Cited

U.S. PATENT DOCUMENTS

| | | | |
|---|---|---|---|
| 3,383,411 | 5/1968 | Schultz et al. | 560/36 |
| 4,058,559 | 11/1977 | Jones et al. | 562/436 |
| 4,072,705 | 2/1978 | Mievylle | 560/36 |
| 4,242,358 | 12/1980 | Wajoie | 260/501.11 |

*Primary Examiner*—G. T. Breitenstein

*Attorney, Agent, or Firm*—Gildo E. Fato; Robert L. Niblack

[57] ABSTRACT

Described are compounds of the formula

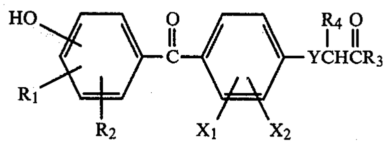

wherein $R_1$ is 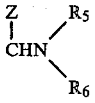

wherein Z is hydrogen or loweralkyl, $R_5$ and $R_6$ may be the same or different and are hydrogen, loweralkyl or together are alkylene of 4 or 5 carbon atoms, $R_2$ is hydrogen, halo, haloloweralkyl, loweralkyl, loweralkoxy, loweralkylthio or

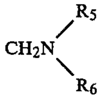

wherein $R_5$ and $R_6$ are previously defined, $R_3$ is hydroxy, alkoxy, branched alkoxy, adamantyloxy, morpholino, amino or amino substituted by loweralkyl or alkylene of 4 or 5 carbon atoms, $R_4$ is hydrogen or loweralkyl, and $X_1$ and $X_2$ are hydrogen, loweralkyl, halo or when substituted on adjacent carbon atoms of the benzene ring form a 1,3-butadienylene linkage, Y is oxygen or sulfur, and pharmaceutically acceptable salts thereof. The compounds are effective as diuretic agents in increasing urinary excretion.

28 Claims, No Drawings

HYDROXYAMINOMETHYL DERIVATIVES OF BENZOYL DI-SUBSTITUTED α-PHENOXYALKANOYL ESTERS

BACKGROUND OF THE INVENTION

This application is a continuation-in-part of U.S. Ser. No. 83,008, filed Oct. 9, 1979, now abandoned.

DETAILED DESCRIPTION OF THE INVENTION

The present invention is directed to compounds of the formula

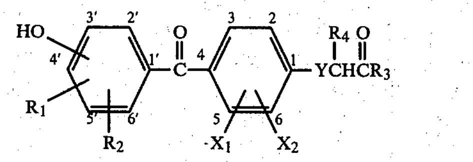

I wherein $R_1$ is

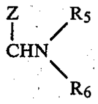

wherein Z is hydrogen or loweralkyl and $R_5$ and $R_6$ may be the same or different and are hydrogen, loweralkyl or together are alkylene or 4 or 5 carbon atoms, $R_2$ is hydrogen, halo, haloloweralkyl, loweralkyl, loweralkoxy, loweralkylthio or

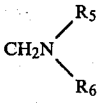

wherein $R_5$ and $R_6$ are as previously defined, $R_3$ is hydroxy, alkoxy, branched alkoxy, adamantyloxy, morpholino, amino or amino substituted by loweralkyl or alkylene of 4 or 5 carbon atoms, $R_4$ is hydrogen or loweralkyl, and $X_1$ and $X_2$ are hydrogen, loweralkyl, halo or when substituted on adjacent carbon atoms of the benzene ring form a 1,3-butadienylene linkage, Y is oxygen or sulfur, and pharmaceutically acceptable salts thereof. The compounds are useful in increasing diuresis in warmblooded animals.

The compounds of formula I may be further classified as having the formula

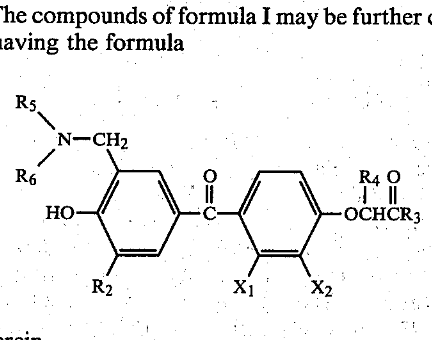

II wherein $R_2$ is hydrogen, halo, haloloweralkyl, loweralkyl, loweralkoxy or loweralkylthio, $R_3$ is hydroxy, loweralkoxy, branched loweralkoxy, adamantyloxy, morpholino, amino or amino substituted by loweralkyl or alkylene of 4 or 5 carbon atoms, $R_4$ is hydrogen or loweralkyl, $R_5$ and $R_6$ are hydrogen, loweralkyl or alkylene of 4 or 5 carbon atoms, and $X_1$ and $X_2$ are hydrogen, loweralkyl, halo or when substituted on adjacent carbon atoms of the benzene ring for a 1,3-butadienylene linkage, or of the formula

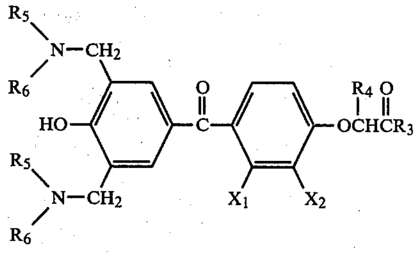

wherein $R_3$ is hydroxy, alkoxy, branched alkoxy, adamantyloxy, morpholino, amino or amino substituted by loweralkyl or alkylene of 4 or 5 carbon atoms, $R_4$ is hydrogen or loweralkyl, $R_5$ and $R_6$ are hydrogen, loweralkyl or alkylene of 4 or 5 carbon atoms, and $X_1$ and $X_2$ are hydrogen, loweralkyl, halo or when substituted on adjacent carbon atoms of the benzene ring form a 1,3-butadienylene linkage.

The term "loweralkyl" as used herein refers to straight or branched chain alkyl radicals containing from 1 to 6 carbon atoms including but not limited to methyl, ethyl, n-propyl, iso-propyl, n-butyl, sec-butyl, 2-methyhexyl, n-pentyl, 1-methylbutyl, 2,2-dimethylbutyl, 2-methylpentyl, 2,2-dimethylpropyl, n-hexyl and the like.

The term "loweralkoxy" as used herein refers to straight or branched chain alkyl radicals containing from 1 to 6 carbon atoms, attached to an oxygen atom.

The term "halo" as used herein refers to chloro, bromo, fluoro and iodo.

The term "pharmaceutically acceptable salts" includes non-toxic acid addition salts of the compounds of Formulas II or III which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, and like salts. Also included are metallic salts such as the sodium or potassium salt of the acid.

The present compounds may be administered to warm-blooded animals orally or parenterally. They can generally be administered with a pharmaceutical carrier. The term "pharmaceutical carrier," for the purpose of the present invention, is intended to refer to any medium that is suitable for the preparation of a dosage unit form, and thus includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For oral administration, amounts of from about 0.1 to 200 mg/kg per day per patient are useful, with the total dose of about 3 gms. per day being a suitable range for large animals, including humans. The whole dosage range described increases the total urinary excretion from about 2 to about 10 fold in most animals. From these figures, it is apparent that the new diuretic compounds are particularly effective in increasing urinary excretion in most animals.

For all dosage forms, the above exemplified compounds can be placed in capsules, formulated into pills, wafers or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

In order to illustrate the manner in which the above compounds may be prepared and the properties of the compounds, reference is made to the following examples, which, however, are not meant to limit or restrict the scope of the invention in any respect.

The following is a general procedure for the preparation of mono and bis dialkylaminomethyl derivatives of 2,3-dichloro-4-(4'-hydroxybenzoyl)phenoxyacetic acid.

2,3-Dichloro-4-(4'-hydroxybenzoyl)phenoxyacetic acid, prepared as described in U.S. Pat. No. 4,058,559, issued Nov. 15, 1977, is slurried with ethanol (1 l./mole of acid). 2 Moles of secondary amine is added to the slurry in one portion. The reaction mixture is stirred to give a solution to which is added a mixture of 1 mole formaldehyde and 2 moles secondary amine if "mono" product is desired. 2.5 Moles formaldehyde and 3 moles secondary amine is added if the "bis" product is desired. The reaction mixture is heated to reflux for 16 to 24 hours, cooled to give product. If product does not precipitate, the reaction solution is concentrated in vacuo to give a glass. The glass is taken up in water, made acid (pH about 4), to give a solid on standing. The crude solid is recrystallized from a suitable solvent to give product.

EXAMPLE 1

Ethyl 2,3-Dichloro-4-(4'-hydroxybenzoyl)phenoxyacetate 85.38 g. (0.25 mole) of 2,3-dichloro 4-(4'-hydroxybenzoyl)-phenoxyacetic acid, 34.5 g. (0.75 mole) of ethanol, and 100 ml. of ethylene dichloride, using 3.5 ml. of sulfuric acid as the catalyst were mixed and refluxed with stirring overnight according to the procedure of Clinton and Laskowski, J.A.C.S. 70 3135, 1948. The acid gradually went into solution. The reaction layer was cooled, separated and the organic layer washed successively with water, twice with $KHCO_3$ solution and finally with water. The dried ethylene dichloride was evaporated to dryness to give an oil which solidified to give 86 g. crude ester on trituration with pentane and filtering; m.p. 127°-9° (93% yield). This material was used without further purification in subsequent experiments.

EXAMPLE 2

Ethyl 2,3-dichloro-4-[(3'-chloro-4'-hydroxy)benzoyl]phenoxyacetate

A mixture of 50 ml. ethylene dichloride and 9.2 g. (0.025 mole) of ethyl 2,3-dichloro-4-(4'-hydroxybenzoyl)phenoxyacetate was treated with 2.5 g. (0.03 mole) of $SO_2Cl_2$. The mixture was heated on a steam bath at reflux for 6 hours. The solvent was removed to give a white solid. This was collected with the aid of ether to give 8.5 g. of a solid; m.p. 135°-40°. Recrystallization with toluene with Darco gave 4.5 g. of the product; m.p. 152°-155°.

Analysis Calcd. for: $C_{17}H_{13}Cl_3O_5$=403.65; C, 50.59; H, 3,24; Cl, 26.35. Found: C, 50.55; H, 3.12; Cl, 25.80.

EXAMPLE 3

2,3-Dichloro-4-[(3'-chloro-4'-hydroxy)benzoyl]phenoxyacetic acid

A solution of 10.09 g. (0.025 mole) of ethyl 2,3-dichloro-4-[(3'-chloro-4'-hydroxy)benzoyl]phenoxyacetate in 37.5 ml. of 2 N NaOH (3 g. in 37.5 ml. $H_2O$) was stirred and heated at 90°-98° for $1\frac{1}{4}$ hours. The solution was cooled to about 50° and acidified with 6 N HCl. A white solid precipitated which was filtered, washed with water and dried to give 9.0 g.; m.p. 104°-111° (dec.) Recrystallization with hot acetic acid and adding water to cloudy point. Cooling gave product, m.p. 190°-191°, 8.69 g. (92.5%).

EXAMPLE 4

Ethyl-2,3-dichloro-4-(4'-methoxybenzoyl)phenoxy-α-methylacetate

A solution of 9.96 (0.055 mole) of ethyl 2-bromopropionate in 12 ml. of acetone was added over a period of 2 hours to a stirred, refluxing mixture of 14.85 g. (0.05 mole) of 2,3-dichloro-4-(4'-methoxybenzoyl)phenol and 7.60 g. (0.055 mole) of powdered anhydrous potassium carbonate in 200 ml. of acetone. After the addition, the mixture was refluxed for 20 hours and the hot mixture was filtered. The filtrate was evaporated in vacuo and the residue was taken up in 250 ml. of chloroform. The chloroform solution was washed with 10% aqueous potassium carbonate, water, dried over anhydrous sodium carbonate and evaporated in vacuo to give the product.

EXAMPLE 5

2,3-Dichloro-4-(4'-hydroxybenzoyl)phenoxy-α-methylacetic acid

A mixture of 19.34 g. of ethyl 2,3-dichloro-4-(4'-methoxybenzoyl)phenoxy-α-methylacetate and 330 ml. of 48% hydrogen bromide was rapidly stirred and refluxed for $21\frac{1}{2}$ hours. The mixture was cooled in an ice bath and diluted with 415 ml. of water, with stirring. The product was filtered and washed with ice water; m.p. 208°-212°.

EXAMPLE 6

Ethyl 2,3-dichloro-4-[(3'-dimethylaminomethyl-4'-hydroxy)-benzoyl]phenoxyacetate hydrochloride A suspension of 2,3-dichloro 4-(4'-hydroxybenzoyl)-phenoxyacetic acid, 34 g. (0.1 mole) was taken into solution by adding 20 ml. of 40% aqueous dimethylamine (0.2 mole). This solution was treated dropwise with a mixture of 20 ml. of dimethylamine and 10 ml. of 37% formaldehyde. The reaction solution was heated at reflux overnight. The reaction was concentrated to give a glass. This was taken up in DMF but no product precipitated. The DMF was removed in vacuo and the residue taken up in water. The water solution deposited on off-white solid. Yield of crude solid was 22.5 g., m.p.

250°-4° dec. The crude solid was triturated with hot DMF and cooled. The product was vacuum dried to give 17 g., m.p. 265°-268° dec. This material was converted to the ethyl ester by suspending in 300 ml. ethanol and adding 20 ml. (excess) thionyl chloride dropwise. This was refluxed overnight. The solution was concentrated in vacuo to give a solid which was recrystallized from ethanol to yield 19.0 g. product, m.p. 186°-188°, 41% of theory.

Analysis Calcd. for $C_{20}H_{22}Cl_3NO_5$=462.761; C, 51.92; H, 4.79; N, 3.02. Found: C, 51.67; H, 5.00; N, 3.01.

EXAMPLE 7

2,3-Dichloro-4[(3'-dimethylaminomethyl-4'-hydroxy)-benzoyl]phenoxyacetic acid To a solution of ethyl 2,3-dichloro-4-[(3'-dimethylaminomethyl-4'-hydroxy)benzoyl]phenoxyacetate hydrochloride (13 g., 0.028 mole) in 150 ml. formic acid 88% was added 6.0 g. (0.061 mole) of methanesulfonic acid. This resulting solution was heated on a steam bath for about 16 hours. The solution was concentrated to give a glass. This glass was taken up in water and treated with $NaHCO_3$ solution (2%) until the solution became cloudy. Standing gave a white solid. Yield was 10.5 g. (91%) m.p. 268°-70° dec.

Analysis Calcd. for: $C_{18}H_{17}Cl_2NO_5$=398.25; C, 54.29; H, 4.30; N, 3.52. Found: C, 54.55; H, 4.30; N, 3.56.

EXAMPLE 8

Ethyl 2,3-dichloro-4-[(3'-diethylaminomethyl-4'-hydroxy)-benzoyl]phenoxyacetate A solution of 18.1 g. (0.03 mole) of ethyl 2,3-dichloro-4-(4'-hydroxybenzoyl)phenoxyacetate and 4.3 g. (0.033 mole) of N-ethoxymethyl diethylamine in 40 cc. of 1,2-dimethoxyethane (monoglyme) was refluxed for 4 hours. At the end of this time, the reaction mixture was concentrated and the resulting gum was taken up in ether and filtered. The ether solution was treated with ethereal HCl and after filtering and drying 14 g. of a slightly hygroscopic hydrochloride salt was obtained. The product was recrystallized from acetonitrile and ether mixture, m.p. 115°-120°.

Analysis Calcd. for $C_{22}H_{25}Cl_2NO_5$.HCl. C, 53.84; H, 5.34; N, 2.85. Found: C, 53.35; H, 5.54; N, 3.05.

EXAMPLE 9

Ethyl 2,3-dichloro-4-{[3'-(1-pyrrolidinylmethyl)-4'-hydroxy]-benzoyl}phenoxyacetate hydrochloride To a stirred solution of 11.07 g. (0.03 mole) of ethyl 2,3-dichloro-4-(4'-hydroxybenzoyl)phenoxyacetate in 50 ml. of ethanol, cooled in an ice bath, there was added dropwise of a previously prepared solution (made by adding slowly 2.5 ml. (0.033 mole) of 37% formaldehyde solution to a stirred solution of 2.14 g (0.03 mole) of pyrrolidine in 10 ml. of ethanol, cooled in an ice bath). After the addition, the mixture was refluxed for 4½ hours and evaporated in vacuo. The residue was extracted with ether. The ether extract was evaporated in vacuo and the residue was purified by chromatography on a Florisil column (100-200 mesh) and eluted with chloroform and then graded chloroform-ethanol mixtures. The produce was isolated as a hydrochloride, m.p. 149°-152° (from ethanol-ether).

Analysis Calcd. for $C_{22}H_{23}Cl_2NO_5$.HCl. C, 54.06; H, 4.95; N, 2.87. Found: C, 54.18; H, 5.31; N, 2.84.

EXAMPLE 10

Ethyl 2,3-dichloro-4-[3'-piperidinomethyl-4'-hydroxy)benzoyl]phenoxyacetate hydrochloride 37% Formaldehyde solution (2.5 ml., 0.33 mole) was added to a solution of 2.55 g. (0.03 mole) of piperidine in 40 ml. ethanol. To this solution was added 11.07 g. (0.03 mole) of ethyl 2,3-dichloro-4-(4'-hydroxybenzoyl)-phenoxyacetate and 20 ml. of ethanol. The mixture was refluxed for 13 hours and evaporated in vacuo. The residue was extracted with ether. The ether extract was evaporated and the residue was purified by chromatography on a Florisil column (100-200 mesh) and eluted with graded chloroform-ethanol mixtures. The product was isolated as a hydrochloride, m.p. 109°-111° (dec) (from ethanol-ether).

Analysis Calcd. for $C_{23}H_{25}Cl_2NO_5$.HCl C, 54.94; H, 5.21; N, 2.79. Found: C, 54.97; H, 5.86; N, 2.43.

EXAMPLE 11

2,3-Dichloro-4-[(4'-hydroxy-3'-morpholinomethyl)benzoyl]phenoxyacetic acid

A mixture of morpholine (0.1 mole, 9.0 ml.) and paraformaldehyde (0.05 mole, 1.5 g.) was suspended in 100 ml. of cyclohexane and t-butanol (1:1). The mixture was heated for two hours and the water formed was removed by a Dean-Stark trap. The mixture was treated with 17 g. (0.05 mole) of 2,3-dichloro 4-(4'-hydroxybenzoyl)phenoxyacetic acid dissolved in 50 ml. DMF. After refluxing for 16 hours, the solvents were removed in vacuo to give a solid. This solid was collected with the aid of ethanol to give 7.5 g. white tan solid, m.p. 263°-265° (dec.) A second crop of solid was obtained by concentrating the mother liquor to dryness. The residue was taken up in water and neutralized with 1 N HCl to give 4.5 g. white solid, m.p. 259°-260° dec. The two fractions were combined and recrystallized from minimum amount of DMF (250 ml.) and adding water to cloudy point. Yield of solid was 9.0 g., m.p. 274°-6° dec. Yield was 41% of theory.

Analysis Calcd. for $C_{20}H_{19}Cl_2NO_6$=440.283. C, 54.56; H, 4.35; N, 3.18. Found: C, 54.33; H, 4.07 N, 3.71.

EXAMPLE 12

Ethyl 2,3-dichloro-4-[(4'-hydroxy-3'-thiomorpholinomethyl)-benzoyl]phenoxyacetate, S,S-dioxide 11.1 g. (0.03 mole) of the ethyl 2,3-dichloro 4-(4'-hydroxybenzoyl)phenoxyacetate 4.056 g. (0.03 mole) of thiomorpholine sulfone, 2.5 g. (0.033 mole) 37% formalin and 60 ml. of 3 A alcohol were refluxed for 20 hours and then allowed to set and cool. A gum separated, which was triturated with ether to give 7 g. of colorless solid, softened 160° C., melted at 173°-177° C. The solid was taken up in 100 ml. boiling acetone and filtered, then concentrated to 50 ml. and ether was added to cloudiness to yield 6 g. of product, m.p. 184°-185° C.

Analysis Calcd. for $C_{22}H_{23}Cl_2NO_7S$: C, 50.78; H, 5.23; N, 2.69. Found: C, 50.50; H, 4.71; N, 3.14.

EXAMPLE 13

Ethyl 2,3-dichloro-4-[(4'-hydroxy-3'-morpholinomethyl)benzoyl]phenoxyacetate, hydrochloride A suspension of 2,3-dichloro-4-[(4'-hydroxy-3'-morpholinomethyl)benoyl]phenoxyacetic acid (0.02 mole, 9.0 g.) in ethanol was treated dropwise with 10 ml. of thionyl chloride. This solution was heated at reflux for 2 hours, cooled overnight and concentrated in vacuo to give a glass. This glass could not be made to solidify. The yield of glass was 9.3 g. Yield was 93% theory.

Analysis Calcd. for $C_{22}H_{24}Cl_3NO_6$=504.798. C, 52.35; H, 4.79; N, 2.77. Found: C, 52.22; H, 4.90; N, 2.89.

EXAMPLE 14

2,3-Dichloro-4-[(4'-hydroxy-3'-sarcosylmethyl)benzoyl]phenoxyacetic acid

A mixture of sarcosine (0.22 mole, 19.6 g.) paraformaldehyde (0.11 mole, 3.3 g.), and 100 ml. of cyclohexane/t-butanol was heated to reflux. To this mixture was added 2,3-dichloro-4-(4'-hydroxybenzoyl)phenoxyacetic acid (0.05 mole, 17 g.) dissolved in 50 ml. DMF. The reaction mixture was refluxed overnight (16 hours) and the solvents were removed in vacuo to give a gum. This gum was taken up in water and the solution was made acid with 6 N HCl to cause precipitation of a solid. This solid could not be recrystallized from any suitable solvent. The yield of solid was 3.5 g. (16%), m.p. 230°–235° dec. Because of its insolubility, this compound was converted to its diethyl ester hydrochloride salt in the next step.

EXAMPLE 15

Ethyl 2,3-dichloro-4-[(3'-ethylsarcosylmethyl-4'-hydroxy)-benzoyl]phenoxyacetate, hydrochloride A suspension of 2,3-dichloro-4-[(4'-hydroxy-3'-sarcosylmethyl)benzoyl]phenoxyacetic acid, (3.5 g., 0.008 mole) in 100 ml. ethanol was treated dropwise with 10 ml. of thionyl chloride. This mixture was heated at reflux for 16 hours, cooled, concentrated in vacuo to give a glass which on drying overnight in vacuo at 80° gave a solid. Yield was 3.6 g., m.p. 198°–201° (dec.). The solid was recrystallized by dissolving in ethanol, concentrating to give a glass and then triturating with hot ethyl acetate to give 3.0 g. product, m.p. 200°–202° (dec.).

Analysis Calcd. for $C_{23}H_{26}Cl_3NO_7$=534.825. C, 51.65; H, 4.90; N, 2.62. Found: C, 51.76; H, 4.93; N, 2.66.

EXAMPLE 16

2,3-Dichloro-4-[(3'-chloro-5'-dimethylaminomethyl-4'-hydroxy)benzoyl]phenoxyacetic acid A mixture of paraformaldehyde (0.05 mol, 1.5 g.) and 20 ml. (0.2 mole) of 40% aqueous dimethylamine and 50 ml. each of t-butanol and cyclohexane were refluxed and water removed with a Dean-Stark trap. This resulting solution was treated with 8.0 g. (0.02 mole) of 2,3-dichloro-4-[(3'-chloro-4'-hydroxy)benzoyl]-phenoxyacetic acid and 50 ml. of DMF. This mixture was refluxed overnight. The solution was concentrated in vacuo to give a solid. This solid was collected with aid of ethanol to give 3.0 g. product, m.p. 225°–228° (dec.). A second crop was obtained from the ethanol mother liquor, yield was 5.0 g., m.p. 75°–100° (dec.). Second crop solid was dissolved in water and heated to give a cloudy solution. To this solution was added glacial acetic acid. A white solid precipitated. This solid was collected and washed with ethanol and finally with ether to give 4.0 g. product, m.p. 221°–223° (dec.). This solid was recrystallized by dissolving in aqueous 2% $KHCO_3$ and precipitating by adding glacial acetic acid. This solid melted 223°–225° (dec.) and gave 2.7 g.

Analysis Calcd. for $C_{18}H_{16}Cl_3NO_5$=432.69. C, 49.67; H, 3.73; N, 3.23. Found: C, 49.64; H, 3.79; N, 3.20.

EXAMPLE 17

Ethyl 2,3-dichloro-4-[(3'-chloro-5'-dimethylaminomethyl-4'-hydroxybenzoyl]phenoxyacetate, hydrochloride To a mixture of 3 g. of 2,3-dichloro-4-[(3'-chloro-5'-dimethylaminomethyl-4'-hydroxy)benzoyl]phenoxyacetic acid in 50 ml. of ethanol was added dropwise 6 ml. (excess) thionyl chloride. After the addition the mixture was heated on the steam bath to give a solution. The solvent was removed in vacuo to give a white solid. This was recrystallized from acetone-ether (1:1) to give product, m.p. 178°–179.5° (dec.).

Analysis Calcd. for $C_{20}H_{21}Cl_4NO_5$=497.206. C, 48.31; H, 4.26; N, 2.82. Found: C, 48.63; H, 4.38; N, 2.92.

EXAMPLE 18

2,3-Dichloro-4-{[3',5'-bis-(dimethylaminomethyl)-4'-hydroxy]benzoyl}phenoxyacetic acid, dihydrochloride A solution of 40% aqueous dimethylamine (0.4 mole), 40 ml. and 37% formaldehyde solution (0.2 mole) 20 ml. was treated with 2,3-dichloro-4-(4'-hydroxybenzoyl)-phenoxyacetic acid (0.05 mole) 17 g. This mixture was heated on a steam bath to give a light amber solution. This solution was heated on a steam bath overnight. The amber solution was concentrated in vacuo and azeotroped with toluene (50 ml.) to give a grey-brown solid. This crude solid was triturated with ethanol (hot) and collected on a Bucher funnel to give yellow solid. This was air dried to give 23.5 g., m.p. 165°–170° (dec.). Recrystallizing first from DMF and then from ethanol-water (1:1) and finally from DMF gave 13.8 g., m.p. 215°–217° (dec.).

Analysis Calcd. for $C_{21}H_{24}Cl_2N_2O_5$.1.5 $H_2O$=411.457. C, 52.29; H, 5.64; N, 5.80. Found: C, 52.07; H, 5.53; N, 5.95.

The base above (2 g.) was converted to the dihyrochloride salt as follows: The base (2 g.) was dissolved in glacial acetic acid and etheral HCl was added in excess. The flask was warmed on steam bath to drive off excess HCl and the dihydrochloride salt was precipitated by adding ether to give a gum. This gum was taken up in acetonitrile to give on cooling a white solid, m.p. 221°–223° (dec.). Yield was 2.3 g.

Analysis Calcd. for $C_{21}H_{26}Cl_4N_2O_5$=528.263 C, 47.75; H, 4.96; N, 5.30; Cl, 26.85. Found: C, 47.89; H, 5.09; N, 5.19; Cl, 27.11.

EXAMPLE 19

Ethyl 2,3-dichloro-4-{[3',5'-bis-(dimethylaminomethyl)-4'-hydroxy]benzoyl}phenoxyacetate, dihydrochloride 2,-Dichloro-4-{[3',5'-bis-(dimethylaminomethyl)-4'-hydroxy]benzoyl}phenoxyacetic acid (54 g., 0.13 mole) was placed into a 1 liter round bottom, three-necked flask, equipped with a mechanical stirrer, an additional funnel and a reflux condenser. To this flask was introduced 500 ml. of absolute N.F. ethanol. The stirred suspension was treated with 50 ml. (0.7 mole) thionyl chloride in a slow steam over a 15 minute period. The heat of reaction caused refluxing and reflux was maintained by heating on a steam bath. Reflux was continued for 2½ hours. The mixture was cooled in an ice water bath to given on collection and washing first with ethanol and finally with ethyl ether a white solid (platelets). These were dried in vacuo to give 59 g. (82%) product, m.p. 208°-210° (dec.). Recrystallizing with 1 liter ethanol containing 10 ml. of thionyl chloride two additional times gave product, m.p. 222°-224° (dec.). Yield of final purified product was 23.5 g. (33%).

Analysis Calcd. for $C_{23}H_{28}Cl_2N_2O_5.2HCl=556.32$. C, 49.66; H, 5.44; N, 5.05. Found: C, 49,74, H, 5.68; N, 5.08.

EXAMPLE 20

Ethyl 2,3-dichloro-4-{[3',5'-bis-(dimorpholinomethyl)-4'-hydroxy]benzoyl}phenoxyacetate, dihydrochloride A mixture of morpholine (about 0.4 mole, 36 ml.) and paraformaldehyde (0.22 mole, 6.6 g.) in a solution of 100 ml. cyclohexane and 100 ml. t-butanol was heated to reflux on an oil bath. The water formed was removed by a Dean-Stark trap. After the theoretical amount of water had been removed (about 2 hours), the flask was allowed to cool and a solution of 17 g. (0.05 mole) of 2,3-dichloro-4-[(4'-hydroxy)benzoyl]phenoxyacetic acid in 50 ml. of DMF was added. The reaction mixture was refluxed overnight. The reaction was cooled in an ice bath to give 12.0 g. (44%) of product, m.p. 175°-185° (dec.). This product was recrystallized from absolute ethanol to give 9 g. product, m.p. 188°-191° (dec.). This solid was suspended in ethanol and 10 ml. (excess) of thionyl chloride was added dropwise with stirring. The solution was refluxed for 4 hours, cooled and concentrated in vacuo to give a glass. This glass could not be made to crystallize. Yield of glass was 10 g. (93%).

Analysis Calcd. for $C_{27}H_{34}Cl_4N_2O_7=640.39$. C, 50.64; H, 5.35; N, 4.38. Found: C, 50.45; H, 5.50; N, 4.27.

EXAMPLE 21

2,3-Dichloro-4-{[3',5'-bis(1-pyrrolidinylmethyl)-4'-hydroxy]benzoyl}phenoxyacetic acid 37% Formaldehyde solution (7.5 ml., 0.1 mole) was added dropwise to a stirred solution of 17.05 g. (0.05 mole) of 2,3-dichloro-4-(4'-hydroxybenzoyl)phenoxyacetic acid and 14.22 g. (0.2 mole) of pyrrolidine in 80 ml. of ethanol. The mixture was stirred and refluxed for 6 hours and more 37% formaldehyde solution (3.75 ml.) was added dropwise and the mixture was refluxed for 18½ hours. After evaporation in vacuo, the residue was triturated with ether and recrystallized from 2-butanone-ethanol, m.p. 233°-236°.

EXAMPLE 22

Ethyl 2,3-dichloro-4-{[3',5'-bis(1-pyrrolidinylmethyl)-4'-hydroxy]benzoyl}phenoxyacetate dihydrochloride Thionyl chloride (5.71 g., 0.048 mole) was added dropwise to a stirred suspension of 4.85 (0.0096 mole) of 2,3-dichloro-4-{[3',5'-bis(1-pyrrolidinylmethyl)-4'-hydroxy]benzoyl}phenoxyacetic acid in 100 ml. of ethanol, cooled in an ice bath. After the addition, the mixture was refluxed for 3 hours and evaporated to dryness in vacuo. The residue was triturated with ether and recrystallized from ethanol, m.p. 171°-173° (dec.).

Analysis Calcd. for $C_{27}H_{32}Cl_2N_2O_5.2HCl$. C, 53.30; H, 5.63; N, 4.61. Found: C, 52.70; H, 5.75; N, 4.48.

EXAMPLE 23

2,3-Dichloro-4-{[3',5'-bis(piperidinomethyl)-4'-hydroxy]benzoyl}phenoxyacetic acid 37% Formaldehyde solution (7.5 ml., 0.1 mole) was added dropwise to a stirred solution of 17.05 g. (0.05 mole) of 2,3-dichloro-4-(4'-hydroxybenzoyl)phenoxyacetic acid and 17.03 g. (0.2 mole) of piperidine in 80 ml. of ethanol. The mixture was heated at 95°-100° for 2½ hours and more 37% formaldehyde solution (3.75 ml.) was added and the mixture was kept at 96° for 15 hours. After evaporation in vacuo, the residue was triturated with ether and recrystallized from dimethylformamide; m.p. 201°-205°.

EXAMPLE 24

Ethyl 2,3-dichloro-4-{[3',5'-bis(piperidinomethyl)-4'-hydroxy]benzoyl}phenoxyacetate dihydrochloride Thionyl chloride (9.64 g., 0.061 mole) was added dropwise to a stirred suspension of 8.70 g. (0.0162 mole) of 2,3-dichloro-4-{[3',5'-bis(piperidinomethyl)-4'-hydroxy]benzoyl}phenoxyacetic acid in 150 ml. of ethanol, cooled in an ice bath. The mixture was refluxed for 3½ hours and evaporated to dryness in vacuo. The residue was triturated with ether and recrystallized from ethanol, m.p. 185°-188° (dec.).

Analysis Calcd. for $C_{29}H_{36}Cl_2N_2O_5.2HCl$: C, 54.72; H, 6.02; N, 4.40. Found: C, 53.99; H, 6.06; N, 4.35.

EXAMPLE 25

Ethyl 2,3-dichloro-4-{[3',5'-bis(thiomorpholinomethyl)-4'-hydroxy]benzoyl}phenoxyacetate, S,S,S',S'-tetraoxide A mixture of 8.1 g. (0.06 mole) of thiomorpholine sulfone and 1.8 g. (0.06 mole) of formalin (5 g. of a 37% solution) were mixed while cooling to form the intermediate methylol compound. To this mixture was added 5.55 g. (0.15 mole) of [2,3-dichloro-4-(4'-hydroxybenzoyl)phenoxy]acetic acid ethyl ester in 30 ml. of 3 A alcohol. The mixture was stirred and refluxed for 23 hours. The reaction mixture was filtered while still hot. The resulting solid was washed well with a 50/50 mixture of alcohol and ether and finally with ether. 8.5 g. was obtained, m.p. 228°-230° (81% yield). The basic Mannich product was recrystallized from 2-butanone, m.p. 228°-230°.

Analysis Calcd. for $C_{27}H_{32}Cl_2N_2O_9S_2$: C, 48.87; H, 4.86; N, 4.22. Found: C, 48.74; H, 5.02; N, 4.05.

EXAMPLE 26

Esters of 2,3-dichloro-4-{[3',5'-bis(dimethylaminomethyl)-4'-hydroxy]benzoyl}phenoxyacetic acid The esters are prepared in the following manner. Thionyl chloride (0.63 ml.) was added to a slurry of 2,3-dichloro-4-[3',5'-bis(dimethylaminomethyl)-4'-hydroxybenzoyl]phenoxyacetic acid (2 g.) in dry dimethylformamide (15 ml.) with stirring under a nitrogen atmosphere. The solid dissolved. After 5 minutes the alcohol (amount specified below) was added. The solution was heated at 70°-75° for 16-18½ hours. The solution was cooled and concentrated in vacuo to give a white solid. The solid was dissolved in a methanol/dichloromethane/concentrated ammonium hydroxide solution in the ratio of 20/80/1. A white precipitant of ammonium chloride formed. The solution was filtered through silica gel (10 g., 80-230 mesh) using the same solvent ratio to elute. The solvent was removed in vacuo to yield a gum. The gum was dissolved in methylene chloride and treated with anhydrous hydrogen chloride gas with cooling. The resultant white solid was isolated by filtration. The solid was dried in vacuo to yield pure ester dihydrochloride salt.

| Alcohol | Amount Used | Yield | Melting Point |
|---|---|---|---|
| Octanol | 2.77 ml. | 1.151 g./40.9% | 205-6° Dec. ↑ |
| Benzyl alcohol | 1.83 ml. | 0.928 g./33.9% | 202-4° Dec. ↑ |
| n-Pentanol | 1.90 ml. | 0.950 g./36% | 210-12° Dec. ↑ |
| 2,2-Dimethylpropanol | 1.547 g. | 0.910 g./34.6% | 226-8° Dec. ↑ |
| Cyclohexylmethanol | 2.16 ml. | 2.250 g./81.9% | 230-1° Dec. ↑ |
| Benzhydrol | 3.2353 g. | 0.897 g./29.4% | 206-7° Dec. ↑ |

Elemental Analysis: Octyl ester: Calculated for: $C_{29}H_{42}Cl_4N_2O_5$ C, 54.38; H, 6.61; N, 4.37; Cl, 22.14. Found: C, 54.62; H, 6.81; N, 4.37; Cl, 22.50.

Elemental Analysis: Benzyl ester: Calculated for: $C_{28}H_{32}Cl_4N_2O_5$ C, 54.38; H, 5.22; N, 4.53; Cl, 22.93. Found: C, 54.00; H, 5.35; N, 4.44; Cl, 24.30.

Elemental Analysis: n-Pentyl ester: Calculated for: $C_{26}H_{36}Cl_4N_2O_5$ C, 52.19; H, 6.06; N, 4.68; Cl, 23.70. Found: C, 52.37; H, 6.28; N, 4.76; Cl, 23.92.

Elemental Analysis: 2,2-Dimethylpropyl ester: Calculated for: $C_{26}H_{36}Cl_4N_2O_5$ C, 52.19; H, 6.06; N, 4.68; Cl, 23.70. Found: C, 52.07; H, 6.31; N, 4.82; Cl, 23.53.

Elemental Analysis: Cyclohexylmethyl ester: Calculated for: $C_{28}H_{38}Cl_4N_2O_5.\frac{1}{2}H_2O$ C, 53.09; H, 6.21; N, 4.42; Cl, 22.39. Found: C, 52.73; H, 6.12; N, 4.43; Cl, 21.77.

Elemental Analysis: Benzhydryl ester: Calculated for: $C_{34}H_{36}Cl_4N_2O_5$ C, 58.80; H, 5.23; N, 4.03; Cl, 20.42. Found: C, 58.84; H, 5.34; N, 3.96; Cl, 22.02.

EXAMPLE 27

Methyl 2,3-dichloro-4-{[3',5'-bis(dimethylaminomethyl)-4'-hydroxy]benzoyl}phenoxyacetate dihydrochloride Thionyl chloride (2.6 ml.) was added dropwise to a stirred slurry of 2,3-dichloro-4-{[3',5'-bis(dimethylaminomethyl)-4'-hydroxy]benzoyl}phenoxyacetic acid (8 g.) in dry dimethylformamide (1 ml.) and dry methanol (60 ml.) under a nitrogen atmosphere. The mixture was heated at reflux for 6 hours. The solution was cooled and the solvent removed in vacuo to yield a white solid. The solid was recrystallized from methanol to yield 2.75 g. (28.9%) of the pure methyl ester dihydrochloride; m.p. 214°-215°.

Analysis Calcd. for $C_{22}H_{28}Cl_4N_2O_5$: C, 48.73; H, 5.20; N, 5.17; Cl, 26.15. Found: C, 48.83; H, 5.39; N, 5.24; Cl, 26.36.

EXAMPLE 28

Ethyl 2,3-dichloro-4-{[3',5'-bis(dimethylaminomethyl)-4'-hydroxy]benzoyl}phenoxyacetate dihydrochloride Thionyl chloride (50 ml.) was added over 15 minutes to a stirred slurry of 2,3-dichloro-4-{[3',5'-bis(dimethylaminomethyl)-4'-hydroxy]benzoyl}phenoxyacetic acid (54 g.) in absolute ethanol (500 ml.). The addition brought the solution to reflux. The refluxing was maintained by external heating for 1½ hours. The mixture was cooled in an ice bath and filtered. The solid was washed with cold ethanol and diethyl ether. The crude solid was recrystallized twice from ethanol (1 liter) containing thionyl chloride (10 ml.) to give 23.5 g. (33%) of the pure ethyl ester dihydrochloride; m.p. 222°-224°.

Analysis Calcd. for $C_{23}H_{28}Cl_4N_2O_5$: C, 49.66; H, 5.44; N, 5.05. Found: C, 49.74; H, 5.68; N, 5.08.

EXAMPLE 29

Isopropyl 2,3-dichloro-4-{[3',5'-bis(dimethylaminomethyl)-4'-hydroxy]benzoyl}phenoxyacetate dihydrochloride Thionyl chloride (10 ml.) was added to a mixture of 2,3-dichloro-4-{[3',5'-bis(dimehtylaminomethyl)-4'-hydroxy]benzoyl}phenoxyacetic acid (3.8 g.) and isopropyl alcohol (200 ml.). The mixture was heated at reflux for 2 hours. Dimethylformamide (20 ml.) was added. Refluxing was continued overnight. The solution was cooled (ice bath) and filtered to give 3.8 g. of a solid material. The solid was recrystallized by dissolving the crystals in hot dimethylformamide (50 ml.), adding isopropyl alcohol (50 ml.), cooling and adding diethyl ether (50 ml.). Filtration of the cold mixture yielded 2.5 g. (52.5%) of the pure isopropyl ester dihydrochloride; m.p. 212°-213°.

Analysis Calcd. for $C_{24}H_{32}Cl_4N_2O_5$: C, 50.54; H, 5.66; N, 4.91. Found: C, 50.49; H, 5.88; N, 4.95.

EXAMPLE 30

Adamantyl 2,3-dichloro-4-{[3',5'-bis(dimethylaminomethyl)-4'-hydroxy]benzoyl}phenoxyacetate, dihydrochloride Thionyl chloride (0.95 ml.) was added dropwise to a slurry of 2,3-dichloro-4-{[3',5'-bis(dimethylaminomethyl)-4'-hydroxy]benzoyl}phenoxyacetic acid (3 g.) and 1-adamantanol (4.013 g.) in dry dimethylformamide (23 ml.) with stirring under a nitrogen atmostphere. The slurry was heated to 70° C. during which the solids dissolved. The reaction was heated at 70°±3° C. for 6 hours, cooled to room temperature and concentrated in vacuo to yield a white solid. The solid was taken up in water and extracted with diethyl ether. The aqueous layer was made basic (pH about 10) with concentrated ammonium hydroride. The basic solution was extracted with dichloromethane. The dichloromethane extracts were dried ($MgSO_4$), filtered and concentrated in vacuo to yield a gum. The gum was dissolved in dichloromethane (25 ml.). The solution was cooled (ice bath) and treated with dry hydrogen chloride gas. A white solid formed and then dissolved. The solution was concentrated to dryness to yield 0.928 g. of the adamantyl ester dihydrochloride as a white powder; m.p. 243°-244° (dec.).

Analysis Calcd. for $C_{32}H_{40}Cl_4N_2O_5.\frac{1}{2}H_2O$: C, 55.45; H, 6.15; N, 4.17; Cl, 21.12. Found: C, 55.43; H, 6.09; N, 4.06; Cl, 21.67.

The aminomethyl derivatives of 4-(hydroxybenzoyl)-phenoxyacetic acid are prepared as follows:

These compounds are prepared by reaction of 4-(hydroxybenzoyl)phenoxyacetic acids with 2-chloro-N-(hydroxymethyl)acetamide or other amidoalkylating agents in the presence of acetic acid and sulfuric acid, sulfuric acid, or methanesulfonic acid to form amidoalkylated product followed by hydrolysis of the amido group and formation of the esters.

EXAMPLE 31

Ethyl 2,3-dichloro-4-[(3'-aminomethyl-4'-hydroxy)benzoyl]-phenoxyacetate hydrochloride 2-Chloro-N-(hydroxymethyl)acetamide (2.72 g., 0.022 mole) was added, in small portions, to a stirred solution of 6.82 g. (0.02 mole) of 2,3-dichloro-4-(4'-hydroxybenzoyl)phenoxyacetic acid in 135 ml. acetic acid and 15 ml. concentrated sulfuric acid at 57°. The mixture was stirred at 57° for ½ hour, then at room teperature for 3 hours and poured into ice water. The gummy solid was separated and refluxed with 50 ml. of ethanol and 10 ml. of concentrated hydrochloride for 6 hours. After evaporation in vacuo, the residue was recrystallized from ethanol and ether. After refrigeration overnight, crystalline solid separated which was removed by filtration. To the filtrate was added more ether and the mixture was kept in cold room for several days. The solid was collected and recrystallized from ethanol and ether; m.p. 200°–210°.

Analysis Calcd. for $C_{18}H_{17}Cl_2NO_5.HCl$: C, 49.73; H, 4.17; N, 3.22. Found: C, 49.50; H, 4.31; N, 3.18.

EXAMPLE 32

Ethyl 2,3-dichloro-4-{[3',5'-bis(aminomethyl)-4'-hydroxy]-benzoyl}phenoxyacetate dihydrochloride 2-Chloro-N-(hydroxymethyl)acetamide (5.44 g., 0.044 mole) was added, in small portions, to a stirred solution of 6.82 g. (0.02 mole) of 2,3-dichloro-4-(4'-hydroxybenzoyl)phenoxyacetic acid in 135 ml. acetic acid and 15 ml. concentrated sulfuric acid at 57°. After stirring at 57° for ½ hour and at room temperature for 3 hours, the mixture was poured into ice water. The gummy solid was separated and refluxed with 100 ml. of ethanol and 20 ml. of concentrated hydrochloric acid for 10 hours. After evaporation in vacuo, the residue was recrystallized twice from ethanol and ether; m.p. 225°–230° (dec.).

Analysis Calcd. for $C_{19}H_{20}Cl_2N_2O_5.2HCl$: C, 45.62; H, 4.43; N, 5.60. Found: C, 45.92; H, 4.48; N, 5.58.

EXAMPLE 33

Ethyl 2,3-dichloro-4-[(3'-aminomethyl-4'-hydroxy-5'-chloro)-benzoyl]phenoxyacetate hydrochloride 2-Chloro-N-(hydroxymethyl)acetamide (2.59 g., 0.021 mole) was added, in small portions, to a stirred solution of 7.51 g. (0.02 mole) of 2,3-dichloro-4-(3'-chloro-4'-hydroxybenzoyl)phenoxyacetic acid in 35 ml. methanesulfonic acid at 40°–50°. After the addition, the mixture was stirred and heated in an oil bath at 95° for 3¾ hours. On cooling, the mixture was poured into water; the solid was filtered and washed with water. The crude product was stirred and refluxed with 75 ml. of ethanol and 15 ml. of concentrated hydrochloric acid for 5 hours. The solid was filtered and recrystallized twice from ethanol; m.p. 224°–226°.

Analysis Calcd. for $C_{18}H_{15}Cl_3NO_5.HCl$: C, 46.08; H, 3.65; N, 2.99. Found: C, 45.90; H, 3.69; N, 2.99.

EXAMPLE 34

2,3-Dichloro-4-{[3'-(2-chloroacetamido)methyl)-4'-hydroxy]benzoyl}phenoxyacetic acid 2-Chloro-N-(hydroxymethyl)acetamide (5.44 g., 0.044 mole) was added, in small portions, to a stirred solution of 13.64 g. (0.04 mole) of 2,3-dichloro-4-(4'-hydroxybenzoyl)phenoxyacetic acid in 120 ml. concentrated sulfuric acid, cooled in an ice bath. The mixture was stirred at room temperature overnight and poured into 1 liter of ice water. The crude product was filtered, washed with ice water and used for the next experiment.

EXAMPLE 35

Ethyl 2,3-dichloro-4-[(3'-aminomethyl-4'-hydroxy-5'-iodo)-benzoyl]phenoxyacetate hydrochloride A solution of 3.57 g. (0.022 mole) of iodine monochloride in 10 ml. of acetic acid was added dropwise to a stirred solution of 8.92 g. (0.02 mole) of crude 2,3-dichloro-4-{[3'-(2-chloroacetamido)methyl-4'-hydroxy]benzoyl}phenoxyacetic acid in 100 ml. acetic acid at 75°–80°. The mixture was stirred at 75°–80° for 20 hours and evaporated in vacuo to dryness. The residue, after trituration with water, was stirred and refluxed with 100 ml. of ethanol and 20 ml. of concentrated hydrochloric acid for 7 hours. After cooling, the product was filtered and recrystallized from ethanol; m.p. 215°–218° (dec.).

Analysis Calcd. for $C_{18}H_{16}Cl_2INO_5.HCl$: C, 38.56; H, 3.06; N, 2.50. Found: C, 38.33; H, 3.03; N, 2.54.

EXAMPLE 36

Ethyl 2,3-dichloro-4-[(3'-aminomethyl-4'-hydroxy)benzoyl]-phenoxy-α-methylacetate 2-Chloro-N-(hydroxymethyl)acetamide (11.11 g., 0.09 mole) was added, in small portions, to a stirred solution of 15.98 g. (0.045 mole) of 2,3-dichloro-4-(4'-hydroxybenzoyl)phenoxy-α-methylacetic acid in 270 ml. acetic acid and 30 ml. concentrated sulfuric acid at 45°–50°. The mixture was stirred at 45° for ½ hour and at room temperature for 2 hours and poured into 1.5 liters of ice water. The gummy solid was separated and refluxed with 200 ml. of ethanol and 40 ml. of concentrated hydrochloric acid for 18 hours. After evaporation in vacuo, the residue was crystallized from ethanol and ether. After refrigeration overnight, the solid was removed by filtration. To the filtrate was added ether and the solution was kept cold. The solution was decanted and evaporated in vacuo. The residue was neutralized with potassium bicarbonate solution and extracted with methylene chloride. The extract was washed with water, dried with anhydrous sodium sulfate and evaporated to dryness. The residue was recrystallized from ethanol; m.p. 122°–124°.

Analysis Calcd. for $C_{19}H_{19}Cl_2NO_5$: C, 55.35; H, 4.65; N, 3.40. Found: C, 55.57; H, 4.58; N, 3.53.

EXAMPLE 37

2,3-Dichloro-4-[(3'-aminomethyl-4'-hydroxy)benzoyl]-phenoxyacetic acid hydrochloride 2-Chloro-N-(hydroxymethyl)acetamide (5.44 g., 0.044 mole) was added, in small portions, to a stirred solution of 13.64 g. (0.04 mole) of 2,3-dichloro-4-(4'- hydroxybenzoyl)phenoxyacetic acid in 60 ml. methanesulfonic acid, cooled in an ice bath. The mixture was stirred at room temperature for 24 hours and poured into ice water. The solid was filtered, washed thoroughly with water, and hydrolysed by heating with 125 ml. of 10% aqueous hydrochloric acid for 10 hours. After cooling, the crude product was collected and recrystallized with 2 N hydrochloric acid; m.p. 237°-240° (dec.).

Analysis Calcd. for $C_{16}H_{13}Cl_2NO_5.HCl$: C, 47.25; H, 3.47; N, 3.44. Found: C, 47.49; H, 3.51; N, 3.35.

EXAMPLE 38

Ethyl 2,3-dimethyl-4-[(3'-Aminomethyl-4'-hydroxy)benzoyl]-phenoxyacetate hydrochloride 2-Chloro-N-(hydroxymethyl)acetamide (1.23 g., 0.01 mole) was added portionwise to a stirred solution of 3.0 g. (0.01 mole) of 2,3-dimethyl-4-(4'-hydroxybenzoyl)-phenoxyacetic acid in 35 ml. concentrated sulfuric acid, cooled in an ice bath. The mixture was stirred at ice bath temperature for 2 hours, then at room temperature for 25 hours, and poured into ice water. The solid was filtered, washed with water, and recrystallized from 1:1 aqueous acetic acid. The amidoalkylated product (1.24 g.) was refluxed with 15 ml. of ethanol and 3 ml. of concentrated hydrochloric acid for 17 hours. The mixture was evaporated to dryness in vacuo and the residue was recrystallized twice from ethanol and ether to give the pure product; m.p. 204°-207° (dec.).

Analysis Calcd. for $C_{20}H_{23}NO_5.HCl$: C, 60.99; H, 6.14; N, 3.56. Found: C, 60.29; H, 6.19; N, 3.54.

EXAMPLE 39

2,3-Dichloro-4-[(3'-aminomethyl-4'-hydroxy-5'-methyl)benzoyl]phenoxyacetate hydrochloride 2-Chloro-N-(hydroxymethyl)acetamide (1.48 g., 0.012 mole) was added, in small portions, to 2,3-dichloro-4-[(4'-hydroxy-3'-methyl)benzoyl]-phenoxyacetic acid in 25 ml. of concentrated sulfuric acid, cooled in an ice bath. The mixture was stirred at room temperature for 17 hours and poured into ice water. The solid was filtered, washed with water, and hydrolysed by heating with 30 ml. of 10% hydrochloric acid for 21 hours. After cooling to room temperature, the product was collected; yield 3.54 g. The ethyl ester was obtained by passing hydrogen chloride to a stirred suspension of the above acid (3.54 g.) in refluxed for 3 hours. After cooling, the ethyl ester hydrochloride was filtered and recrystallized from ethanol; m.p. 231°-233° (dec.)

Analysis Calcd. for: $C_{19}H_{19}Cl_2NO_5.HCl$: C, 50.85; H, 4.49; N, 3.12. Found: C, 50.72; H, 4.51; N, 3.11.

EXAMPLE 40

4-(4-Nitrobenzoyl) anisole

A mixture of anisole (8.67 g., 0.08 mole), 4-nitrobenzoyl chloride (16.4 g., 0.088 mole) and methylene chloride (80 ml). at 5° was stirred vigorously and treated with finely powdered aluminum chloride (11.2 g., 0.084 mole). The reaction mixture was stirred at room temperature for 20 hrs. and then decomposed with ice and hydrochloric acid (15 ml.). The aqueous solution was extracted twice with methylene chloride. The combined methylene chloride solution was washed with aqueous sodium bicarbonate solution and finally with water. The organic layer was dried ($MgSO_4$) and filtered. The solvent was removed in vacuo, and the residue on triturating with methanol gave the product, m.p. 121°-122°. This product was used in the next step without purification. 4-(4-nitrobenzoyl)-2-chloroanisole and 4-(4-nitrobenzoyl)-3-chloroanisole were prepared by the same procedure.

EXAMPLE 41

4-(4-Nitrobenzoyl) phenol

A mixture of 4-(4-nitrobenzoylanisole (15.5 g.), prepared by the method of Example 40, 48% hydrobromic acid (50 ml.), and acetic acid (125 ml.) was heated at reflux for 30 hrs. and then allowed to cool to room temperature. The crystalline solid which had formed was collected by filtration to yield 11.8 g. of product m.p. 194°-6°. This was used as such for the next step. Prepared by the same procedure were:
4-(4-nitrobenzoyl)-2-chlorophenol and
4-(4-nitrobenzoyl-3-chlorophenol.

EXAMPLE 42

Ethyl 4-(4-nitrobenzoyl) phenoxy acetate

A mixture of 4-(4-nitrobenzoyl) phenol (11.8 g., 0.0486 mole) prepared by the method of Example 41, ethyl bromoacetate (8.92 g., 0.0534 mole) and anhydrous potassium carbonate (7.38 g., 0.0534 mole) in acetone (115 ml.) was heated at reflux for 17 hrs. and then filtered. The filtrate was partially evaporated and the residue was dissolved in methylene chloride. The organic solution was washed with aqueous sodium chloride and dried over magnesium sulfate. The solvent was evaporated to give a solid product. This material was recrystallized from ethanol to give 12.6 g. of product, m.p. 108°-109°. Ethyl 4-(4-nitrobenzoyl)-2-chlorophenoxy acetate and ethyl 4-(4-nitrobenzoyl)-3-chlorophenoxy acetate were analogously prepared.

EXAMPLE 43

4-(4-Hydroxybenzoyl) phenoxy acetic acid

To a suspension of sodium hydride (4.32 g., 0.09 mole, 50% suspension in mineral oil) in 50 ml. of dimethylformamide was added by dropwise addition acetaldoxime (5.31 g., 0.09 mole) at 5°. The mixture was stirred for 10 minutes at 20°-25° and then treated by dropwise addition with a solution of 10 g. (0.03 mole) of ethyl 4-(4-nitrobenzoyl) phenoxy acetate in 50 ml. of dimethylformamide. The resulting mixture was stirred at room temperature for 5 hrs. and poured into cold water. Acidification with concentrated hydrochloric gave a solid which was collected by filtration and dried. There was obtained 7 g. of product. This material was used without purification for the next step. In a similar manner were prepared the following two compounds: 4-(4-hydroxybenzoyl)-2-chlorophenoxy acetic acid and 4-(4-hydroxybenzoyl)-3-chlorophenoxy acetic acid.

EXAMPLE 44

Ethyl 4-[(3'-aminomethyl-4'-hydroxy) benzoyl]-phenoxyacetic acid hydrochloride 2-Chloro-N-(hydroxymethyl) acetamide (1.9 g.=0.0154 mole) was added portionwise to a stirred solution of 4 g. (0.0147 mole) of 4-(4-hydroxybenzoyl) phenoxyacetic acid in 35 ml. of concentrated sulfuric acid, cooled to 10° in a cold water bath. The mixture was stirred at 15° for 4 hours, then poured into ice water. The solid was filtered, washed with water and dried. The amidomethylated product (4.7 g.) was dissolved in 150 ml. of ethanol containing 0.75 ml. of concentrated sulfuric acid and allowed to stand for 24 hrs. The ethanol was partially evaporated and the residue dissolved in methylene chloride. The organic solution was washed with aqueous sodium chloride solution, dried ($MgSO_4$) and evaporated to dryness. The residual ethyl ester was chromatographed on silica gel eluting with benzene-ethyl acetate mixtures to give 2.5 g. of the purified amidomethylated product. This was placed in 35 ml. of ethanol and 25 ml. of concentrated hydrochloric acid and heated at reflux for 4 hrs. The solvents were evaporated to dryness and the residue allowed to stand overnight in ethanolic hydrogen chloride. Addition of ether then gave the final product as a white solid, (1.1 g.).

Analysis calculated for $C_{18}H_{19}NO_5.HCl$: C, 59.10; H, 5.51; N, 3.83. Found: C, 58.80; H, 5.65; N, 3.73.

Similarly prepared were: ethyl 2-chloro-4-[(3'-aminometyl-4'-hydroxy) benzoyl]phenoxyacetic acid hydrochloride and ethyl 3-chloro-4-[(3'-aminomethyl-4'-hydroxy) benzoyl]phenoxyacetic acid hydrochloride.

EXAMPLE 45

2,3-Dichloro-4-[(3'-aminomethyl-4'-hydroxy)benzoyl] phenoxyacetamide

To a mixture of ethyl 2,3-dichloro-4-[(3'-aminomethyl-4'-hydroxy)benzoyl] phenoxyacetate hydrochloride (22.8 g., 0.052 mole) and N-benzyloxycarbonyloxysuccinimide (13.5 g., 0.054 mole) in 225 ml. of acetonitrile was added 5.4 g. (0.054 mole) of potassium bicarbonate in 60 ml. of water at 0°-5°. The reaction mixture was allowed to warm to room temperature and stirred an additional 1.5 hrs. The resulting two phase mixture was placed in a separatory funnel and the aqueous layer removed. The organic layer was evaporated under reduced pressure and the residue dissolved in methylene chloride. The methylene chloride solution was washed with aqueous sodium bicarbonate solution and dried over magnesium sulfate. Evaporation of the organic solvent furnished the liquid N-carbobenzoxy derivative which was crystallized from ethyl acetate/hexane to give 22 g., m.p. 117°-119°. A 5 g. portion of the N-carbobenzyloxy compound was dissolved in absolute ethanol and anhydrous ammonia was passed into the solution for 1.5 hrs. After standing overnight at room temperature, the ethanol was evaporated under reduced pressure. The solid residue was dissolved in methyl cellosolve (100 ml.) and the solution acidified with concentrated HCl. The acidic solution was then poured into 350 ml. of cold water and the carboxamide derivative filtered and dried. The CBZ protecting group was removed by dissolving 2 g. of the above amide in 10 ml. of HBr/acetic acid and stirring at room temperature for 35 minutes. Upon pouring this mixture into an excess of ether, the title compound was formed as a white solid. The product was filtered and dried to give 3.5 g. of pure material, m.p. 258°-260°.

Analysis calculated for $C_{16}H_{14}Cl_2N_2O_4.HBr.\frac{1}{2}H_2O$: C, 41.86; H, 3.29; N, 6.10. Found: C, 42.10; H, 3.34; N, 5.90.

EXAMPLE 46

Using the procedure of Example 40, the following compounds were made.

4-(4-Nitrobenzoyl)-3,5-dichloroanisole was prepared by the same procedure as Example 40 except after stirring at room temperature for 20 hrs., the mixture was refluxed for 1 hr.; m.p. of crude product 127°-141° C.

1-Methoxy-4-(4-nitrobenzoyl) naphthalene, m.p. 147°-150° C.

4-(2-Hydroxybenzoyl)-2,3-dichlorophenetole was prepared by reaction of 2-methoxybenzoyl chloride and 2,3-dichlorophenetole; m.p. of crude product 112°-120° C.

EXAMPLE 47

Using the procedure of Example 41 the following compounds were made.

4-(4-Nitrobenzoyl)-3,5-dichlorophenol was prepared by the same procedure as Example 41 except the heating was continued for 24 hrs.; m.p. 118°-120° C.

4-(4-Nitrobenzoyl)-1-naphthol, m.p. of crude product 210°-219° C.

4-(2-Hydroxybenzoyl)-2,3-dichlorophenol was prepared by heating 4-(2-hydroxybenzoyl)-2,3-dichlorophenetole with 3 molar equivalents of aluminum chloride in methylene chloride for 16 hrs.; m.p. 200°-202° C.

EXAMPLE 48

Using the procedure of Example 42, the following compounds were made.

Ethyl 4-(4-nitrobenzoyl)-3,5-dichlorophenoxyacetate was prepared using 2-butanone as a solvent; m.p. 96°-98° C.

Ethyl 4-(4-nitrobenzoyl)-1-naphthoxyacetate; m.p. 121°-123° C.

Ethyl 4-(2-hydroxybenzoyl)-2,3-dichlorophenoxyacetate was prepared by the same procedure using anhydrous sodium bicarbonate and acetone; m.p. 108°-110° C.

EXAMPLE 49

Using the procedure of Example 43, the following compounds were made.

4-(4-Hydroxybenzoyl)-3,5-dichlorophenoxyacetic acid; m.p. 73°-77° C.

4-(4-Hydroxybenzoyl)-1-naphthoxyacetic acid; m.p. 234°-237° C.

4-(2-Hydroxybenzoyl)-2,3-dichlorophenoxyacetic acid was prepared by hydrolysis of ethyl 4-(2-hydroxybenzoyl)-2,3-dichlorophenoxyacetate with potassium hydroxide in ethanol at room temperature; m.p. 201°-203° C.

EXAMPLE 50

Using the procedure of Example 44, the following compounds were made.

Ethyl 4-[(3'-aminomethyl-4'-hydroxy)benzoyl]-1-naphthoxyacetate hydrochloride was prepared as above example except using methanesulfonic acid as solvent at room temperature; m.p. 186°-190° C.

Ethyl 4-[(3'-aminomethyl-4'-hydroxy)benzoyl]-3,5-dichlorophenoxyacetate hydrochloride; m.p. 149°-151° C.

Ethyl 4-[(4'-aminomethyl-2'-hydroxy)benzoyl]-2,3-dichlorophenoxyacetate hydrochloride; m.p. 168°-170° C.

Also made was the compound: Ethyl 4-[3'-(1-aminoethyl)-4'-hydroxy)benzoyl]-phenoxyacetate hydrochloride, m.p. 125° C.

The diuretic activity of the compounds of the invention was established in normotensive rats. In this test, male normotensive rats (Sprague-Dawley), weighing 275–375 grams are used. Groups of eight rats are used for each dose level.

The test drug or control (suspension vehicle) is administered orally (via gavage) to each animal and immediately thereafter the animal is administered saline via oral catheter with 0.9% saline equivalent to 5% of the animal's body weight. The animals are then placed in individual stainless steel metabolism cages. No food or water is given to the rats during the test. Urine volume is measured and recorded and a sample is collected at intervals of 2 hours and six hours after dosing.

When dose ranging studies are done the urine volume is read and recorded at 1, 2, 3, 4, 5, 6, and 24 hours after administration.

Each test compound, control or dose of test compound is tested in eight animals. As a control, the suspension vehicle is given (0.5% methylcellulose) in a volume of 2 ml./kg. body weight.

Drugs are dissolved or suspended in 0.5% methylcellulose so that the appropriate dose is present in 2 ml./kg. body weight. For routine screening a dose of 100 mg./kg. po is typically employed.

For convenience, the compounds tested are identified in Table I with the urine volume obtained at each dose level of compound administered being recorded in Table II.

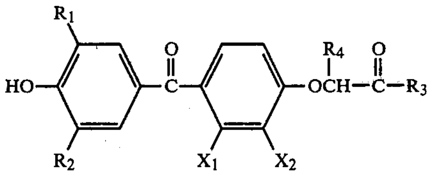

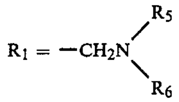

TABLE I

| Compound | $R_1$ | $R_2$ | $R_3$ | $R_4$ | $R_5$ | $R_6$ | $X_1$ | $X_2$ |
|---|---|---|---|---|---|---|---|---|
| 1* | — | H | OH | H | H | H | Cl | Cl |
| 2* | — | H | $OC_2H_5$ | H | H | H | Cl | Cl |
| 3* | — | $(CH_3)_2NCH_2$ | $OC_2H_5$ | H | $CH_3$ | $CH_3$ | Cl | Cl |
| 4* | — | $(CH_3)_2NCH_2$ | OH | H | $CH_3$ | $CH_3$ | Cl | Cl |
| 5[a] | H | Cl | $OC_2H_5$ | H | | | Cl | Cl |
| 6* | — | H | $OC_2H_5$ | H | $CH_3$ | $CH_3$ | Cl | Cl |
| 7 | — | H | OH | H | $CH_3$ | $CH_3$ | Cl | Cl |
| 8[a] | H | H | $OC_2H_5$ | H | | | Cl | Cl |
| 9 | — | Cl | $OC_2H_5$ | H | $CH_3$ | $CH_3$ | Cl | Cl |
| 10* | — | 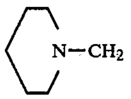 | $OC_2H_5$ | H | | 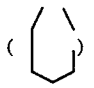 | Cl | Cl |
| 11* | — | 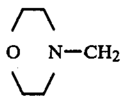 | $OC_2H_5$ | H | | 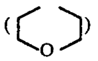 | Cl | Cl |
| 12 | — | Cl | OH | H | $CH_3$ | $CH_3$ | Cl | Cl |
| 13 | — | 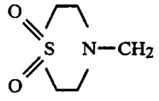 | OH | H | | 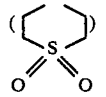 | Cl | Cl |
| 14* | — | Cl | $OC_2H_5$ | H | | 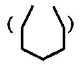 | Cl | Cl |
| 15* | — | 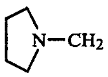 | $OC_2H_5$ | H | | 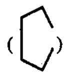 | Cl | Cl |
| 16* | — | H | $OC_2H_5$ | H | | 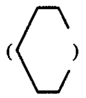 | Cl | Cl |
| 17* | — | H | $OC_2H_5$ | H | | 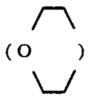 | Cl | Cl |
| 18 | — | 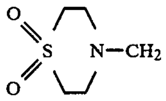 | $OC_2H_5$ | H | | 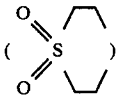 | Cl | Cl |
| 19 | — | H | OH | H | | 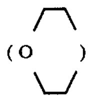 | Cl | Cl |
| 20* | — | H | $OC_2H_5$ | H | $C_2H_5$ | $C_2H_5$ | Cl | Cl |
| 21* | — | H | OH | H | $C_2H_5$ | $C_2H_5$ | Cl | Cl |

TABLE I-continued

| Compound | $R_1$ | $R_2$ | $R_3$ | $R_4$ | $R_5$ | $R_6$ | $X_1$ | $X_2$ |
|---|---|---|---|---|---|---|---|---|
| 22* | — | 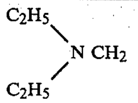 | $OC_2H_5$ | H | $C_2H_5$ | $C_2H_5$ | Cl | Cl |
| 23* | — | H | $OC_2H_5$ | H | $CH_3$ | 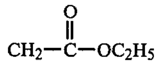 | Cl | Cl |
| 24* | — | H | $OC_2H_5$ | H | | 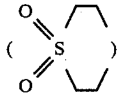 | Cl | Cl |
| 25 | — | H | $OC_2H_5$ | H | | 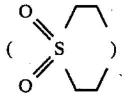 | Cl | Cl |
| 26* | — | H | $OC_2H_5$ | H | | 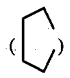 | Cl | Cl |
| 27 | — | Cl | $OC_2H_5$ | H | $CH_3$ | H | Cl | Cl |
| 28* | — | $(CH_3)_2NCH_2$ | $OC_2H_5$ | $CH_3$ | $CH_3$ | $CH_3$ | Cl | Cl |
| 29* | — | $(CH_3)_2NCH_2$ | $OCH(CH_3)_2$ | H | $CH_3$ | $CH_3$ | Cl | Cl |
| 30* | — | $(CH_3)_2NCH_2$ | $OCH_3$ | H | $CH_3$ | $CH_3$ | Cl | Cl |
| 31* | — | $(CH_3)_2NCH_2$ | $O(CH_2)_7CH_3$ | H | $CH_3$ | $CH_3$ | Cl | Cl |
| 32* | — | $(CH_3)_2NCH_2$ | $O(CH_2)_4CH_3$ | H | $CH_3$ | $CH_3$ | Cl | Cl |
| 33* | — | $(CH_3)_2NCH_2$ | $O-CH_2C(CH_3)_3$ | H | $CH_3$ | $CH_3$ | Cl | Cl |
| 34* | — | $(CH_3)_2NCH_2$ | 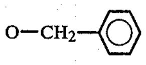 | H | $CH_3$ | $CH_3$ | Cl | Cl |
| 35* | — | $(CH_3)_2NCH_2$ | 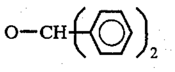 | H | $CH_3$ | $CH_3$ | Cl | Cl |
| 36* | — | $(CH_3)_2NCH_2$ | 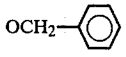 | H | $CH_3$ | $CH_3$ | Cl | Cl |
| 37* | — | $(CH_3)_2NCH_2$ | 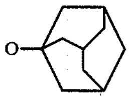 | H | $CH_3$ | $CH_3$ | Cl | Cl |
| 38* | — | H | $O-CH(CH_3)_2$ | H | H | H | Cl | Cl |
| 39* | — | $CH_3$ | $OC_2H_5$ | H | H | H | Cl | Cl |
| 40* | — | H | OH | H | H | H | Cl | Cl |
| 41* | — | H | $OC_2H_5$ | H | H | H | $CH_3$ | $CH_3$ |
| 42* | — | Cl | $OC_2H_5$ | H | H | H | Cl | Cl |
| 43* | — | I | $OC_2H_5$ | H | H | H | Cl | Cl |
| 44 | — | H | $OC_2H_5$ | H | H | H | 1-3-Butadienylene | |
| 45 | — | H | $OC_2H_5$ | $CH_3$ | H | H | Cl | Cl |
| 46 | — | H | $OC_2H_5$ | H | H | H | H | H |
| 47 | — | H | $OC_2H_5$ | H | H | H | H | Cl |
| 48[b] | — | H | $OC_2H_5$ | H | H | H | Cl | Cl |
| 49 | C | H | $OC_2H_5$ | H | H | H | Cl | Cl |
| 50 | — | H | $OC_2H_5$ | H | H | H | 3-Cl | 5-Cl |
| 51 | — | H | $OC_2H_5$ | H | H | H | Cl | H |
| 52 | — | H | $NH_2$ | H | H | H | Cl | Cl |

Note:

—: $R_1$ is 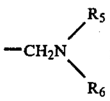 ;

*: HCl salt;
[a]: compounds 5 and 8 represent example 2 and 1 respectively where $R_1$ is H;
[b]: Z is methyl;
[c]: hydroxy is at the 2'-position.

TABLE 2

| COMPOUND | DOSE MG/KG | RTE | LOAD | TIME (HRS) | VOLUME |
|---|---|---|---|---|---|
| 1 | 30 | PO | SAL 5% | 0-2 | 4.47/ |
| | | | | 0-6 | 3.23/ |
| | | | | 0-24 | 1.58/ |
| 2 | 100 | PO | SAL 5% | 0-2 | 4.42/.00* |
| | | | | 0-6 | 3.29/.00* |
| | | | | 0-24 | 2.15/.00* |
| | | | | 2-6 | 2.00/.00* |

TABLE 2-continued

| COMPOUND | DOSE MG/KG | RTE | LOAD | TIME (HRS) | VOLUME |
|---|---|---|---|---|---|
| | | | | 6-24 | 1.05/.61 |
| | 30 | PO | SAL 5% | 0-2 | 5.05/.00* |
| | | | | 0-6 | 3.47/.00* |
| | | | | 0-24 | 2.15/.00* |
| | | | | 2-6 | 1.66/.01* |
| | | | | 6-24 | 0.88/.04* |
| | 10 | PO | SAL 5% | 0-2 | 4.81/.00* |

TABLE 2-continued

| COMPOUND | DOSE MG/KG | RTE | LOAD | TIME (HRS) | VOLUME |
|---|---|---|---|---|---|
| | | | | 0-6 | 3.25/.00* |
| | | | | 0-24 | 1.93/.00* |
| | | | | 2-6 | 1.46//03* |
| | | | | 6-24 | 0.65/.00* |
| | 3 | PO | SAL 5% | 0-2 | 4.68/.00* |
| | | | | 0-6 | 3.22/.00* |
| | | | | 0-24 | 1.86/.00* |
| | | | | 2-6 | 1.53/.02* |
| | | | | 6-24 | 0.54/.00* |
| | 1 | PO | SAL 5% | 0-2 | 4.11/.00* |
| | | | | 0-6 | 2.78/.00* |
| | | | | 0-24 | 1.57/.00* |
| | | | | 2-6 | 1.27/.22 |
| | | | | 6-24 | 0.39/.00* |
| | 0.30 | PO | SAL 5% | 0-2 | 2.41/.00* |
| | | | | 0-6 | 2.06/.00* |
| | | | | 0-24 | 1.27/.01* |
| | | | | 2-6 | 1.66/.01* |
| | | | | 6-24 | 0.51/.00* |
| | 0.10 | PO | SAL 5% | 0-2 | 1.11/58 |
| 3 | 100 | PO | SAL 5% | 0-2 | 7.20/.00* |
| | | | | 0-6 | 3.34/.00* |
| | | | | 2-6 | 1.12/.46 |
| | 100 | PO | SAL 5% | 0-2 | 5.51/.00* |
| | | | | 0-6 | 3.40/.00* |
| | | | | 0-24 | 1.79/.00* |
| | | | | 2-6 | 1.58/.02* |
| | | | | 6-24 | 0.41/.00* |
| | 30 | PO | SAL 5% | 0-2 | 4.64/.00* |
| | | | | 0-6 | 2.92/.00* |
| | | | | 0-24 | 1.57/.00* |
| | | | | 2-6 | 1.43/.03* |
| | | | | 6-24 | 0.41/.00* |
| | 10 | PO | SAL 5% | 0-2 | 3.23/.00* |
| | | | | 0-6 | 2.31/.00* |
| | | | | 0-24 | 1.28/.00* |
| | | | | 2-6 | 1.52/.06 |
| | | | | 6-24 | 0.40/.00* |
| | 3 | PO | SAL 5% | 0-2 | 1.84/.03* |
| | | | | 0-6 | 1.57/.00* |
| | | | | 0-24 | 1.10/.18 |
| | | | | 2-6 | 1.33/.08 |
| | | | | 6-24 | 0.71/.00* |
| | 1 | PO | SAL 5% | 0-2 | 0.60/.11 |
| | | | | 0-6 | 0.89/.34 |
| | | | | 0-24 | 0.96/.58 |
| | | | | 2-6 | 1.14/.41 |
| | | | | 6-24 | 1.03/.81 |
| 4 | 100 | IV | SAL 5% | 0-2 | 6.16/.00* |
| | | | | 0-6 | 3.79/.00* |
| | | | | 2-6 | 2.15/.00* |
| | 100 | PO | SAL 5% | 0-2 | 1.17/.60 |
| | | | | 0-6 | 0.99/.96 |
| | | | | 2-6 | 0.83/.39 |
| 5 | 100 | PO | SAL 5% | 0-2 | 1.64/.13 |
| | | | | 0-6 | 1.29/.07 |
| | | | | 2-6 | 1.16/.33 |
| 6 | 100 | PO | SAL 5% | 0-2 | 4.05/.00* |
| | | | | 0-6 | 3.03/.00* |
| | | | | 2-6 | 1.89/.00* |
| | 30 | PO | SAL 5% | 0-2 | 5.02/.00* |
| | | | | 0-6 | 2.75/.00* |
| | | | | 0-24 | 1.52/.00* |
| | | | | 2-6 | 1.08/.60 |
| | | | | 6-24 | 0.32/.00* |
| | 10 | PO | SAL 5% | 0-2 | 3.22/.00* |
| | | | | 0-6 | 1.83/.00* |
| | | | | 0-24 | 1.13/.04* |
| | | | | 2-6 | 0.80/.11 |
| | | | | 6-24 | 0.46/.00* |
| | 3 | PO | SAL 5% | 0-2 | 1.78/.01* |
| | | | | 0-6 | 1.41/.01* |
| | | | | 0-24 | 1.03/.62 |
| | | | | 2-6 | 1.14/.32 |
| | | | | 6-24 | 0.67/.01* |
| | 1 | PO | SAL 5% | 0-2 | 0.77/.30 |
| | | | | 0-6 | 0.99/.92 |
| 7 | 1 | PO | SAL 5% | 0-24 | 0.98/.74 |
| | | | | 2-6 | 1.15/.37 |
| | | | | 6-24 | 0.98/.85 |

TABLE 2-continued

| COMPOUND | DOSE MG/KG | RTE | LOAD | TIME (HRS) | VOLUME |
|---|---|---|---|---|---|
| | 100 | PO | SAL 5% | 0-2 | 1.33/.53 |
| | | | | 0-6 | 1.52/.02* |
| | | | | 2-6 | 1.61/.00* |
| 8 | 100 | PO | SAL 5% | 0-2 | 1.48/.20 |
| | | | | 0-6 | 1.45/.03* |
| | | | | 2-6 | 1.44/.03* |
| 9 | 100 | PO | SAL 5% | 0-2 | 4.76/.00* |
| | | | | 0-6 | 3.11/.00* |
| | | | | 2-6 | 1.90/.00* |
| | 300 | PO | SAL 5% | 0-2 | 6.59/.00* |
| | | | | 0-6 | 4.07/.00* |
| | | | | 0-24 | 2.38/.00* |
| | | | | 2-6 | 2.74/.00* |
| | | | | 6-24 | 1.11/.20 |
| | 100 | PO | SAL 5% | 0-2 | 7.57/.00* |
| | | | | 0-6 | 4.22/.00* |
| | | | | 6-24 | 2.17/.00* |
| | | | | 2-6 | 2.45/.00* |
| | | | | 6-24 | 0.64/.00* |
| | 30 | PO | SAL 5% | 0-2 | 6.71/.00* |
| | | | | 0-6 | 3.60/.00* |
| | | | | 0-24 | 1.81/.00* |
| | | | | 2-6 | 1.96/.00* |
| | | | | 6-24 | 0.48/.00* |
| | 10 | PO | SAL 5% | 0-2 | 4.62/.00* |
| | | | | 0-6 | 2.54/.00* |
| | | | | 0-24 | 1.36/.00* |
| | | | | 2-6 | 1.43/.05* |
| | | | | 6-24 | 0.49/.00* |
| | 3 | PO | SAL 5% | 0-2 | 3.56/00* |
| | | | | 0-6 | 1.92/.00* |
| | | | | 0-24 | 1.11/.14* |
| | | | | 2-6 | 1.05/.74 |
| | | | | 6-24 | 0.50/.00* |
| 10 | 100 | PO | SAL 5% | 0-2 | 0.71/.07 |
| | | | | 0-6 | 0.67/.02* |
| | | | | 2-6 | 0.65/.05* |
| 11 | 100 | PO | SAL 5% | 0-2 | 0.62/.03* |
| | | | | 0-6 | 0.63/.00* |
| | | | | 2-6 | 0.64/.03* |
| 12 | 100 | PO | SAL 5% | 0-2 | 1.19/.36 |
| | | | | 0-6 | 1.23/.06 |
| | | | | 2-6 | 1.26/.09 |
| 13 | 100 | PO | SAL 5% | 0-2 | 0.91/.66 |
| | | | | 0-6 | 0.85/.20 |
| | | | | 2-6 | 0.81/.35 |
| 14 | 100 | PO | SAL 5% | 0-2 | 1.09/.73 |
| | | | | 0-6 | 1.16/.41 |
| | | | | 2-6 | 1.19/.42 |
| 15 | 100 | PO | SAL 5% | 0-2 | 1.38.14 |
| | | | | 0-6 | 1.23/.17 |
| | | | | 2-6 | 1.15/.48 |
| 16 | 100 | PO | SAL 5% | 0-2 | 5.71/.00* |
| | | | | 0-6 | 3.43/.00* |
| | | | | 2-6 | 1.86/.00* |
| | 300 | PO | SAL 5% | 0-2 | 5.59/.00* |
| | | | | 0-6 | 3.36/.00* |
| | | | | 0.24 | 1.89/.00* |
| | | | | 2-6 | 1.74/.00* |
| | | | | 6-24 | 0.59/.01* |
| | 100 | PO | SAL 5% | 0-2 | 5.58/.00* |
| | | | | 0-6 | 3.11/.00* |
| | | | | 0-24 | 1.71/.00* |
| | | | | 2-6 | 1.33/.05* |
| | | | | 6-24 | 0.47/.00* |
| | 30 | PO | SAL 5% | 0-2 | 3.30/.00* |
| | | | | 0-6 | 2.22/.00* |
| | | | | 0-24 | 1.26/.00* |
| | | | | 2-6 | 1.43/.03* |
| | | | | 6-24 | 0.42/.00* |
| | 10 | PO | SAL 5% | 0-2 | 1.32/.45 |
| | | | | 0-6 | 1.48/.01* |
| | | | | 0-24 | 1.11/.13 |
| | | | | 2-6 | 1.58/.00* |
| | | | | 6-24 | 0.77/.09 |
| | 3 | PO | SAL 5% | 0-2 | 1.00/.99 |
| | | | | 0-6 | 1.04/.76 |
| | | | | 0-24 | 1.06/.38 |
| | | | | 2-6 | 1.07/.68 |
| | | | | 6-24 | 1.08/.53 |

TABLE 2-continued

| COMPOUND | DOSE MG/KG | RTE | LOAD | TIME (HRS) | VOLUME |
|---|---|---|---|---|---|
| 17 | 100 | PO | SAL 5% | 0–2 | 4.33/.00* |
| | | | | 0–6 | 3.06/.00* |
| | | | | 2–6 | 1.96/.00* |
| 18 | 100 | PO | SAL 5% | 0–2 | 0.83/.35 |
| | | | | 0–6 | 1.00/.99 |
| | | | | 2–6 | 1.08/.69 |
| 19 | 100 | PO | SAL 5% | 0–2 | 0.72/.13 |
| | | | | 0–6 | 0.78/.13 |
| | | | | 2–6 | 0.84/.36 |
| 20 | 100 | PO | SAL 5% | 0–2 | 5.26/.00* |
| | | | | 0–6 | 3.39/.00* |
| | | | | 2–6 | 1.99/.00* |
| 21 | 100 | PO | SAL 5% | 0–2 | 0.96/.82 |
| | | | | 0–6 | 1.35/.02* |
| | | | | 2–6 | 1.64/.01* |
| 22 | 100 | PO | SAL 5% | 0–2 | 0.90/.56 |
| | | | | 0–6 | 1.31/.00* |
| | | | | 2–6 | 1.61/.00* |
| 23 | 100 | PO | SAL 5% | 0–2 | 0.97/.83 |
| | | | | 0–6 | 1.23/.02* |
| | | | | 2–6 | 1.43/.04* |
| 24 | 100 | PO | SAL 5% | 0–2 | 0.81/.23 |
| | | | | 0–6 | 0.98/.88 |
| | | | | 2–6 | 1.13/.62 |
| 25 | 100 | PO | SAL 5% | 0–2 | 0.50/.00* |
| | | | | 0–6 | 0.80/.12 |
| | | | | 2–6 | 1.06/.75 |
| 26 | 100 | PO | SAL 5% | 0–2 | 5.07/.00* |
| | | | | 0–6 | 3.68/.00* |
| | | | | 2–6 | 2.23/.00* |
| 27 | 100 | PO | SAL 5% | 0–2 | 4.94/.00* |
| | | | | 0–6 | 3.63/.00* |
| | | | | 2–6 | 2.26/.00* |
| 28 | 100 | PO | SAL 5% | 0–2 | 3.49/.00* |
| | | | | 0–6 | 2.10/.00* |
| | | | | 2–6 | 0.92/.63 |
| | 30 | PO | SAL 5% | 0–2 | 1.59/.02* |
| | | | | 0–6 | 1.45/.01* |
| | | | | 2–6 | 1.35/.10 |
| 29 | 100 | PO | SAL 5% | 0–2 | 6.19/.00* |
| | | | | 0–6 | 3.23/.00* |
| | | | | 2–6 | 1.53/.01* |
| | 300 | PO | SAL 5% | 0–2 | 5.09/.00* |
| | | | | 0–6 | 3.57/.00* |
| | | | | 0–24 | 2.12/.00* |
| | | | | 2–6 | 2.22/.00* |
| | | | | 6–24 | 0.89/.47 |
| | 100 | PO | SAL 5% | 0–2 | 5.72/.00* |
| | | | | 0–6 | 3.53/.00* |
| | | | | 0–24 | 1.78/.00* |
| | | | | 2–6 | 1.55/.06 |
| | | | | 6–24 | 0.31/.00* |
| | 30 | PO | SAL 5% | 0–2 | 4.07/.00* |
| | | | | 0–6 | 2.71/.00* |
| | | | | 0–24 | 1.42/.00* |
| | | | | 2–6 | 1.49/.09 |
| | | | | 6–24 | 0.32/.00* |
| | 10 | PO | SAL 5% | 0–2 | 2.22/.01* |
| | | | | 0–6 | 2.04/.00* |
| | | | | 0–24 | 1.21/.04* |
| | | | | 2–6 | 1.87/.02* |
| | | | | 6–24 | 0.51/.00* |
| | 3 | PO | SAL 5% | 0–2 | 1.06/.86 |
| | | | | 0–6 | 1.42/.05* |
| | | | | 0–24 | 1.05/.57 |
| | | | | 2–6 | 1.74/.02* |
| | | | | 6–24 | 0.74/.01* |
| 30 | 100 | PO | SAL 5% | 0–2 | 8.21/.00* |
| | | | | 0–6 | 4.57/.00* |
| | | | | 2–6 | 2.23/.00* |
| | 30 | PO | SAL 5% | 0–2 | 5.19/.00* |
| | | | | 0–6 | 3.12/.00* |
| | | | | 0–24 | 1.39/.00* |
| | | | | 2–6 | 1.48/.07 |
| | | | | 6–24 | 0.30/.00* |
| | 10 | PO | SAL 5% | 0–2 | 3.04/.00* |
| | | | | 0–6 | 2.26/.00* |
| | | | | 0–24 | 1.10/.16 |
| | | | | 2–6 | 1.64/.00* |
| | | | | 6–24 | 0.38/.00* |

TABLE 2-continued

| COMPOUND | DOSE MG/KG | RTE | LOAD | TIME (HRS) | VOLUME |
|---|---|---|---|---|---|
| | 3 | PO | SAL 5% | 0–2 | 1.46/.13 |
| | | | | 0–6 | 1.37/.02* |
| | | | | 0–24 | 0.94/.39 |
| | | | | 2–6 | 1.29/.12 |
| | | | | 6–24 | 0.67/.00* |
| | 1 | PO | SAL 5% | 0–2 | 1.27/.50 |
| | | | | 0–6 | 1.25/.30 |
| | | | | 0–24 | 1.02/.80 |
| | | | | 2–6 | 1.24/.25 |
| | | | | 6–24 | 0.88/.22 |
| 31 | 100 | PO | SAL 5% | 0–2 | 8.75/.00* |
| | | | | 0–6 | 4.28/.00* |
| | | | | 2–6 | 1.87/.01* |
| | 30 | PO | SAL 5% | 0–2 | 5.34/.00* |
| | | | | 0–6 | 3.28/.00* |
| | | | | 0–24 | 1.42/.00* |
| | | | | 2–6 | 1.88/.04* |
| | | | | 6–24 | 0.31/.00* |
| | 10 | PO | SAL 5% | 0–2 | 3.52/.00* |
| | | | | 0–6 | 2.11/.00* |
| | | | | 0–24 | 1.17/.01* |
| | | | | 2–6 | 1.16/.35 |
| | | | | 6–24 | 0.60/.00* |
| | 3 | PO | SAL 5% | 0–2 | 1.77/.01* |
| | | | | 0–6 | 1.66/.00* |
| | | | | 0–24 | 1.20/.00* |
| | | | | 2–6 | 1.59/.01* |
| | | | | 6–24 | 0.92/.29 |
| | 1 | PO | SAL 5% | 0–2 | 1.43/.25 |
| | | | | 0–6 | 1.56/.02* |
| | | | | 0–24 | 1.12/.04* |
| | | | | 2–6 | 1.65/.00* |
| | | | | 6–24 | 0.86/.15 |
| | 100 | PO | SAL 5% | 0–2 | 8.31/.00* |
| | | | | 0–6 | 4.22/.00* |
| | | | | 2–6 | 2.01/.00* |
| 32 | 30 | PO | SAL 5% | 0–2 | 7.15/.00* |
| | | | | 0–6 | 3.48/.00* |
| | | | | 0–24 | 1.49/.00* |
| | | | | 2–6 | 1.00/.99 |
| | | | | 6–24 | 0.30/.00* |
| | 10 | PO | SAL 5% | 0–2 | 4.53/.00* |
| | | | | 0–6 | 2.25/.00* |
| | | | | 0–24 | 1.13/.04* |
| | | | | 2–6 | 0.70/.01* |
| | | | | 6–24 | 0.46/.00* |
| | 3 | PO | SAL 5% | 0–2 | 1.68/.04* |
| | | | | 0–6 | 1.51/.01* |
| | | | | 0–24 | 1.12/.14 |
| | | | | 2–6 | 1.38/.03* |
| | | | | 6–24 | 0.89/.37 |
| | 1 | PO | SAL 5% | 0–2 | 1.08/.75 |
| | | | | 0–6 | 1.23/.16 |
| | | | | 0–24 | 1.11/.08 |
| | | | | 2–6 | 1.34/.06 |
| | | | | 6–24 | 1.04/.62 |
| 33 | 100 | PO | SAL 5% | 0–2 | 10.40/.00* |
| | | | | 0–6 | 4.13/.00* |
| | | | | 2–6 | 0.84/.35 |
| | 30 | PO | SAL 5% | 0–2 | 5.62/.00* |
| | | | | 0–6 | 3.12/.00* |
| | | | | 0–24 | 1.35/.00* |
| | | | | 2–6 | 1.14/.45 |
| | | | | 6–24 | 0.23/.00* |
| | 10 | PO | SAL 5% | 0–2 | 3.45/.00* |
| | | | | 0–6 | 1.95/.00* |
| | | | | 0–24 | 1.02/.82 |
| | | | | 2–6 | 0.76/.17 |
| | | | | 6–24 | 0.43/.00* |
| | 3 | PO | SAL 5% | 0–2 | 1.92/.00* |
| | | | | 0–6 | 1.71/.00* |
| | | | | 0–24 | 1.09/21 |
| | | | | 2–6 | 1.54/.01* |
| | | | | 6–24 | 0.70/.00* |
| | 1 | PO | SAL 5% | 0–2 | 1.15/.50 |
| | | | | 0–6 | 1.16/.29 |
| | | | | 0–24 | 0.99/.91 |
| | | | | 2–6 | 1.16/.46 |
| | | | | 6–24 | 0.89/.14 |
| | 100 | PO | SAL 5% | 0–2 | 6.11/.00* |

TABLE 2-continued

| COMPOUND | DOSE MG/KG | RTE | LOAD | TIME (HRS) | VOLUME |
|---|---|---|---|---|---|
| | | | | 0-6 | 3.65/.00* |
| | | | | 2-6 | 1.52/.04* |
| 35 | 100 | PO | SAL 5% | 0-2 | 9.06/.00* |
| | | | | 0-6 | 3.08/.00* |
| | | | | 2-6 | 0.80/.02* |
| 36 | 100 | PO | SAL 5% | 0-2 | 5.16/.00* |
| | | | | 0-6 | 3.07/.00* |
| | | | | 2-6 | 1.17/.43 |
| | 300 | PO | SAL 5% | 0-2 | 3.98/.00* |
| | | | | 0-6 | 2.83/.00* |
| | | | | 0-24 | 1.73/.00* |
| | | | | 2-6 | 1.83/.00* |
| | | | | 6-24 | 0.80/.03* |
| | 100 | PO | SAL 5% | 0-2 | 4.51/.00* |
| | | | | 0-6 | 2.61/.00* |
| | | | | 0-24 | 1.36/.00* |
| | | | | 2-6 | 0.96/.59 |
| | | | | 6-24 | 0.31/.00* |
| | 30 | PO | SAL 5% | 0-2 | 3.03/.00* |
| | | | | 0-6 | 1.81/.01* |
| | | | | 0-24 | 1.00/.99 |
| | | | | 2-6 | 0.75/.13 |
| | | | | 6-24 | 0.32/.00* |
| | 10 | PO | SAL 5% | 0-2 | 1.10/.60 |
| | | | | 0-6 | 1.25/.05* |
| | | | | 0-24 | 1.04/.33 |
| | | | | 2-6 | 1.38/.01* |
| | | | | 6-24 | 0.86/.05* |
| | 3 | PO | SAL 5% | 0-2 | 0.81/.29 |
| | | | | 0-6 | 0.98/.79 |
| | | | | 0-24 | 1.00/.99 |
| | | | | 2-6 | 1.13/.08 |
| | | | | 6-24 | 1.02/.82 |
| 37 | 30 | PO | SAL 5% | 0-2 | 4.49/.00* |
| | | | | 0-6 | 2.63/.00* |
| | | | | 2-6 | 1.46/.00* |
| | 30 | PO | SAL 5% | 0-2 | 5.67/.00* |
| | | | | 0-6 | 3.32/.00* |
| | | | | 0-24 | 1.65/.01* |
| | | | | 2-6 | 1.94/.00* |
| | | | | 6-24 | 0.35/.01* |
| | 10 | PO | SAL 5% | 0-2 | 2.96/.00* |
| | | | | 0-6 | 2.30/.00* |
| | | | | 0-24 | 1.38/.09 |
| | | | | 2-6 | 1.92/.00* |
| | | | | 6-24 | 0.65/.15 |
| | 3 | PO | SAL 5% | 0-2 | 1.87/.01* |
| | | | | 0-6 | 1.98/.00* |
| | | | | 0-24 | 1.20/.34 |
| | | | | 2-6 | 2.04/.00* |
| | | | | 6-24 | 0.60/.09 |
| | 1 | PO | SAL 5% | 0-2 | 2.13/.01* |
| | | | | 0-6 | 1.75/.01* |
| | | | | 0-24 | 1.30/.17 |
| | | | | 2-6 | 1.52/.08 |
| | | | | 6-24 | 0.95/.82 |

Note:
Statistically significant P-values (0.05 or less).

What is claimed is:

1. A compound of the formula

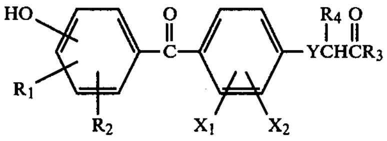

wherein $R_1$ is 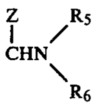

wherein Z is hydrogen or loweralkyl and $R_5$ and $R_6$ may be the same or different and are hydrogen, loweralkyl or together are alkylene of 4 or 5 carbon atoms, $R_2$ is hydrogen, halo, haloloweralkyl, loweralkyl, loweralkoxy, loweralkylthio or

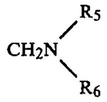

wherein $R_5$ and $R_6$ are as previously defined, $R_3$ is hydroxy, alkoxy, branched alkoxy, adamantyloxy, morpholino, amino or amino substituted by loweralkyl or together are alkylene of 4 or 5 carbon atoms, $R_4$ is hydrogen or loweralkyl, and $X_1$ and $X_2$ are hydrogen, loweralkyl, halo or when substituted on adjacent carbon atoms of the benzene ring form a 1,3-butadienylene linkage, Y is oxygen or sulfur, and pharmaceutically acceptable salts thereof.

2. A compound of the formula

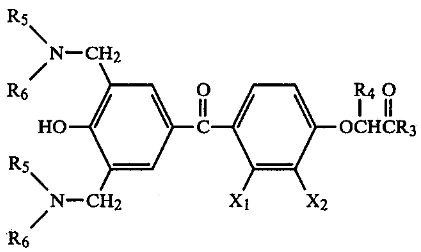

wherein $R_3$ is hydroxy, alkoxy, branched alkoxy, adamantyloxy, morpholino, amino or amino substituted by loweralkyl or together are alkylene of 4 or 5 carbon atoms, $R_4$ is hydrogen or loweralkyl, $R_5$ and $R_6$ are hydrogen, loweralkyl or together are alkylene of 4 or 5 carbon atoms, and $X_1$ and $X_2$ are hydrogen, loweralkyl, halo or when substituted on adjacent carbon atoms of the benzene ring form a 1,3-butadienylene linkage, and pharmaceutically acceptable salts thereof.

3. A compound of claim 2 wherein $R_3$ is ethoxy or isopropoxy, $R_4$ is hydrogen, $R_5$ and $R_6$ are each methyl and $X_1$ and $X_2$ are each chloro.

4. The compound of claim 2 wherein $R_3$ is ethoxy, $R_4$ is hydrogen, $R_5$ and $R_6$ are each hydrogen and $X_1$ and $X_2$ are each chloro.

5. A compound of the formula

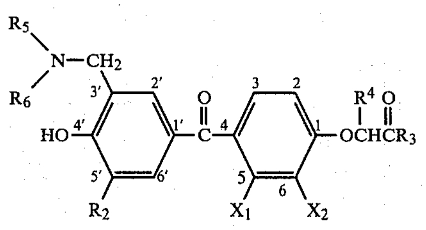

wherein $R_2$ is hydrogen, halo, haloloweralkyl, loweralkyl, loweralkoxy or loweralkylthio, $R_3$ is hydroxy, alkoxy, branched alkoxy, adamantyloxy, morpholino, amino or amino substituted by lower alkyl or together are alkylene of 4 or 5 carbon atoms, $R_4$ is hydrogen or loweralkyl, $R_5$ and $R_6$ are hydrogen, loweralkyl or together are alkylene of 4 or 5 carbon atoms, and $X_1$ and $X_2$ are hydrogen, loweralkyl, halo or when substituted on adjacent carbon atoms of the benzene ring form a 1,3-butadienylene linkage, and pharmaceutically acceptable salts thereof.

6. A compound of claim 5 wherein $R_2$ is hydrogen, $R_3$ is ethoxy, isopropoxy or hydroxy, $R_4$ is hydrogen, $R_5$ and $R_6$ are each hydrogen and $X_1$ and $X_2$ are each chloro.

7. The compound of claim 5 wherein $R_2$ is hydrogen, $R_3$ is ethoxy, $R_4$ is hydrogen, $R_5$ and $R_6$ are each hydrogen and $X_1$ and $X_2$ are each methyl.

8. The compound of claim 5 wherein $R_2$ is methyl, $R_3$ is ethoxy, $R_4$ is hydrogen, $R_5$ and $R_6$ are each hydrogen and $X_1$ and $X_2$ are each chloro.

9. The compound of claim 5 wherein $R_2$ is hydrogen, $R_3$ is ethoxy, $R_4$ is hydrogen, $R_5$ and $R_6$ are each methyl and $X_1$ and $X_2$ are each chloro.

10. The compound of claim 5 wherein $R_2$ is chloro, $R_3$ is ethoxy, $R_4$ is hydrogen, $R_5$ and $R_6$ are each hydrogen and $X_1$ and $X_2$ are each chloro.

11. The compound of claim 5 wherein $R_2$ is iodo, $R_3$ is ethoxy, $R_4$ is hydrogen, $R_5$ and $R_6$ are each hydrogen and $X_1$ and $X_2$ are each chloro.

12. The compound of claim 5 wherein $R_2$ is hydrogen, $R_3$ is ethoxy, $R_4$ is hydrogen, $R_5$ and $R_6$ are each hydrogen and $X_1$ and $X_2$ are each chloro.

13. The compound of claim 5 wherein $R_2$ is hydrogen, $R_3$ is hydroxy, $R_4$ is hydrogen, $R_5$ and $R_6$ are each hydrogen and $X_1$ and $X_2$ are each chloro.

14. The compound of claim 5 wherein $R_2$ is hydrogen, $R_3$ is ethoxy, $R_4$ is hydrogen, $R_5$ and $R_6$ are each ethyl and $X_1$ and $X_2$ are each chloro.

15. The compound of claim 5 wherein $R_2$ is chloro, $R_3$ is ethoxy, $R_4$ is hydrogen, $R_5$ and $R_6$ are each methyl and $X_1$ and $X_2$ are each chloro.

16. The compound of claim 2 wherein $R_3$ is methoxy, $R_4$ is hydrogen, $R_5$ and $R_6$ are each methyl and $X_1$ and $X_2$ are each chloro.

17. The compound of claim 2 wherein $R_3$ is octyloxy, $R_4$ is hydrogen, $R_5$ and $R_6$ are each methyl and $X_1$ and $X_2$ are each chloro.

18. The compound of claim 2 wherein $R_3$ is pentoxy, $R_4$ is hydrogen, $R_5$ and $R_6$ are each methyl and $X_1$ and $X_2$ are each chloro.

19. The compound of claim 2 wherein $R_3$ is isobutoxy, $R_4$ is hydrogen, $R_5$ and $R_6$ are each methyl and $X_1$ and $X_2$ are each chloro.

20. The compound of claim 5 wherein $R_2$ is hydrogen, $R_3$ is ethoxy, $R_4$ is hydrogen, $R_5$ and $R_6$ are each hydrogen, and $X_1$ and $X_2$ together form a 1,3-butadienylene linkage.

21. The compound of claim 5 wherein $R_2$ is hydrogen, $R_3$ is ethoxy, $R_4$ is methyl, $R_5$ and $R_6$ are each hydrogen, and $X_1$ and $X_2$ are each chloro.

22. The compound of claim 5 wherein $R_2$ is hydrogen, $R_3$ is ethoxy, $R_4$ is hydrogen, $R_5$ and $R_6$ are each hydrogen, and $X_1$ and $X_2$ are each hydrogen.

23. The compound of claim 5 wherein $R_2$ is hydrogen, $R_3$ is ethoxy, $R_4$ is hydrogen, $R_5$ and $R_6$ are each hydrogen, $X_1$ is hydrogen, and $X_2$ is chloro.

24. The compound of claim 5 wherein $R_2$ is hydrogen, $R_3$ is ethoxy, $R_4$ is hydrogen, $R_5$ and $R_6$ are each hydrogen, $X_1$ s chloro and $X_2$ is hydrogen.

25. The compound of claim 5 wherein $R_2$ is hydrogen, $R_3$ is amino, $R_4$ is hydrogen, $R_5$ and $R_6$ are each hydrogen, and $X_1$ and $X_2$ are each chloro.

26. The compound of claim 1 wherein $R_2$ is hydrogen, $R_3$ is ethoxy, $R_4$ is hydrogen, $R_5$ and $R_6$ are each hydrogen, $X_1$ is 3-chloro and $X_2$ is 5-chloro.

27. The compound of claim 1 wherein $R_2$ is hydrogen, $R_3$ is ethoxy, $R_4$ is hydrogen, $R_5$ and $R_6$ are each hydrogen, $X_1$ is 3-chloro, $X_2$ is 2-chloro, and the hydroxy is at the 2'-position.

28. The compound of claim 1 wherein $R_2$ is hydrogen, $R_3$ is ethoxy, $R_4$ is hydrogen, Z is methyl, $R_5$ and $R_6$ are each hydrogen and $X_1$ and $X_2$ are each chloro.

* * * * *

UNITED STATES PATENT AND TRADEMARK OFFICE

CERTIFICATE OF CORRECTION

PATENT NO. : 4,323,691

DATED : April 6, 1982

INVENTOR(S) : Carroll W. Ours, et. al.

It is certified that error appears in the above—identified patent and that said Letters Patent is hereby corrected as shown below:

In column 28, line 24, before "alkylene", delete "together are".

In column 28, line 51, before "alkylene", delete "together are".

In column 29, line 17, before "alkylene", delete "together are".

Signed and Sealed this

*Ninth* Day of *August 1983*

[SEAL]

*Attest:*

GERALD J. MOSSINGHOFF

*Attesting Officer* *Commissioner of Patents and Trademarks*